United States Patent
Wilson et al.

(10) Patent No.: US 7,226,910 B2
(45) Date of Patent: Jun. 5, 2007

(54) TREATMENT OF FEMALE SEXUAL DYSFUNCTION WITH VASOACTIVE INTESTINAL POLYPEPTIDE AGONISTS

(75) Inventors: Leland F. Wilson, Menlo Park, CA (US); Virgil A. Place, Kawaihae, HI (US)

(73) Assignee: Vivus, Inc., Mountain View, CA (US)

( * ) Notice: Subject to any disclaimer, the term of this patent is extended or adjusted under 35 U.S.C. 154(b) by 0 days.

(21) Appl. No.: 11/262,067

(22) Filed: Oct. 28, 2005

(65) Prior Publication Data

US 2006/0041021 A1 Feb. 23, 2006

Related U.S. Application Data

(60) Continuation of application No. 09/929,818, filed on Aug. 13, 2001, now abandoned, which is a continuation-in-part of application No. 09/498,522, filed on Feb. 4, 2000, now abandoned, which is a division of application No. 09/181,316, filed on Oct. 27, 1998, now abandoned, which is a continuation-in-part of application No. 08/959,064, filed on Oct. 28, 1997, now Pat. No. 5,877,216, and a continuation-in-part of application No. 08/959,057, filed on Oct. 28, 1997, now abandoned.

(51) Int. Cl.
*A61K 38/00* (2006.01)

(52) U.S. Cl. .............................. 514/12; 514/2; 930/170

(58) Field of Classification Search ..................... None
See application file for complete search history.

(56) References Cited

U.S. PATENT DOCUMENTS

| | | | |
|---|---|---|---|
| 5,217,953 A | 6/1993 | Gozes et al. | |
| 5,376,637 A | 12/1994 | Sawai et al. | |
| 5,428,015 A | 6/1995 | Kurono et al. | |
| 5,565,424 A | 10/1996 | Gozes et al. | |
| 5,612,314 A * | 3/1997 | Stamler et al. | 514/13 |
| 5,877,216 A | 3/1999 | Place et al. | |
| 5,972,883 A | 10/1999 | Gozes et al. | |
| 5,998,368 A | 12/1999 | Gozes et al. | |
| 6,031,002 A | 2/2000 | Wysor et al. | |
| 6,051,555 A | 4/2000 | Hadley | |
| 6,103,765 A | 8/2000 | Neal | |
| 6,217,886 B1 | 4/2001 | Önyüksel et al. | |
| 6,239,107 B1 | 5/2001 | Gozes et al. | |
| 6,266,560 B1 | 7/2001 | Zhang et al. | |
| 6,300,335 B1 | 10/2001 | Campbell et al. | |
| 2005/0075284 A1 | 4/2005 | Gozes et al. | |

FOREIGN PATENT DOCUMENTS

| | | |
|---|---|---|
| EP | 0 295 317 | 12/1988 |
| EP | 0 755 685 | 1/1997 |
| WO | WO 01/17479 | 3/2001 |
| WO | WO 01/90144 | 11/2001 |

OTHER PUBLICATIONS

Jia et al. 1999, European Journal of Pharmacology, vol. 366, pp. 79-86.*
Levin, R.J., *VIP, Vagina, Clitoral and Periurethral Glans—An Update on Human Female Genital Arousal*, Exp. Clin. Endocrinol. 98(2):61-69 (1991).
Ottensen et al., *Vasoactive Intestinal Polypeptide (VIP) Provokes Vaginal Lubrication in Normal Women*, PEPTIDES 8:797-800 (1987).
Ottensen et al., *Influence of Pregnancy and Sex Steroids on Concentration, Motor Effect, and Receptor Binding of VIP in the Rabbit Female Genital Tract*, Regulatory Peptides 11:83-92 (1985).

* cited by examiner

*Primary Examiner*—B. Dell Chism
(74) *Attorney, Agent, or Firm*—Mintz, Levin, Cohn, Ferris, Glovsky and Popeo, P.C.; Carol Schneider; Isaac M. Rutenberg

(57) ABSTRACT

Methods for treating female sexual dysfunction are provided. A pharmaceutical composition containing a vasoactive agent selected from vasoactive intestinal potypeptide (VIP) and VIP agonists is administered to the vagina and/or vulvar region of the individual undergoing treatment. The formulations are also useful for improving vaginal muscle tone and tissue health, enhancing vaginal lubrication, and minimizing excess collagen deposition. Pharmaceutical formulations and kits are also provided.

23 Claims, No Drawings

US 7,226,910 B2

TREATMENT OF FEMALE SEXUAL DYSFUNCTION WITH VASOACTIVE INTESTINAL POLYPEPTIDE AGONISTS

CROSS-REFERENCE TO RELATED APPLICATIONS

This application is a continuation of U.S. patent application Ser. No. 09/929,818, filed on Aug. 13, 2001, now abandoned, which is a continuation-in-part of U.S. patent application Ser. No. 09/498,522, filed Feb. 4, 2000, now abandoned, which is a divisional of U.S. patent application Ser. No. 09/181,316, filed Oct. 27, 1998, now abandoned, which was a continuation-in-part of U.S. patent application Ser. No. 08/959,064, filed Oct. 28, 1997, which issued on Mar. 2, 1999 as U.S. Pat. No. 5,877,216, and which was also a continuation-in-part of U.S. patent application Ser. No. 08/959,057, also filed Oct. 28, 1997, now abandoned, the disclosures of which are hereby incorporated by reference.

TECHNICAL FIELD

This invention relates generally to methods and pharmaceutical formulations for treating female sexual dysfunction, and more particularly relates to vaginal and/or vulvar administration of a vasoactive agent, such as a prostaglandin or a vasoactive intestinal polypeptide, in such treatment. The invention further relates to additional methods of using the present pharmaceutical formulations, including, but not limited to, the prevention of yeast infections and the improvement of vaginal muscle tone.

BACKGROUND OF THE INVENTION

Sexual response in women is generally classified into four stages: excitement, plateau, orgasm, and resolution. Masters and Johnson, *Human Sexual Response* (Little, Brown & Co., Boston, Mass. 1966). With sexual arousal and excitement, vasocongestion and muscular tension increase progressively, primarily in the genitals, and is manifested by increased blood flow, elevated luminal oxygen tension, and vaginal surface lubrication as a result of plasma transudation that saturates the fluid reabsorptive capacity of the vaginal epithelium. Vasoactive intestinal polypeptide ("VIP") release may induce the physiological changes of sexual arousal and excitement, and may be the major neurotransmitter effecting neurologically controlled increase of the vaginal blood supply upon arousal. The peptide histidine methionine has been co-located with VIP within nerve fibers that innervate small blood vessels, smooth muscle, and epithelial cells in the vaginal tract.

VIP is a neurotransmitter known to effect small vessel dilation in the mesenteric blood supply in response to mechanical sensation of food in the gut to promote digestion. VIP is therefore found in the cholinergic, parasympathetic ganglia of the intestinal peripheral nervous system. Kandel, Schwartz, and Jessel, *Principles of Neural Science*, 4$^{th}$ ed. (McGraw-Hill 2000). VIP was initially discovered, isolated and purified from porcine intestine, and the twenty-eight (28) amino acid VIP has extensive homology to secretin and glucagon (Carlquist et al., *Horm. Metab. Res.* 14:28–29 (1982)). VIP is known to exhibit a wide range of biological activities in the gastrointestinal tract and circulatory system. VIP has been shown to stimulate pancreatic and biliary secretion, hepatic glycogenolysis, glucagon and insulin secretion and to activate pancreatic bicarbonate release (Kerrins t al., *Proc. Soc. Exp. Biol. Med.* 142:1014–1017 (1972); Domschke et al., *Gastroenterology* 73:78–480 (1977)).

The physiologic effects of VIP extend outside the digestive system. For example, neurons containing VIP have been localized by immunoassay in cells of the endocrine and exocrine systems, intestine and smooth muscle (Polak et al., *Gut* 15:720–724 (1974)), and has been found to be a neuroeffector of the release of hormones including prolactin (Frawley et al., *Neuroendocrinology* 33:79–83 (1981)), thyroxine (Ahren et al., *Nature* 287:343–345 (1980)), and the aforementioned insulin and glucagon (Schebalin, et al., *Am. J. Physiology E.* 232:197–200 (1977). VIP is present in neurons and neural junctions in the airways of animal species including man (Dey et al., *Fed. Proc.* 39:1062 (1980); Said et al., *Ann. N.Y. Acad. Sciences* 221:103–114 (1974)). VIP has also been found to stimulate renin release from the kidney in vivo and in vitro (Porter et al., *Neuroendocrinology* 36:404–408 (1983)), and the presence of VIP in other parts of the genito-urinary system has been shown. The widely appreciated direct vasoactive effect of VIP is to increase blood flow into capillary bed by dilation of the afferent blood vessel. Various analogs of VIP, both agonistic and antagonistic are known to exist (see, e.g., U.S. Pat. Nos. 5,235,907, 5,141,924, 4,734,400 and 4,605,641 to Bolin; and U.S. Pat. Nos. 4,939,224 and 4,835,252 to Musso et al.).

Sexual excitement is initiated by any of a number of psychogenic or somatogenic stimuli and must be reinforced to result in orgasm. With continued stimulation, excitement progresses in intensity into a plateau stage, from which the individual can shift into orgasm. The orgasmic stage is characterized by a rapid release from vasocongestion and muscular tension.

During the various stages of sexual response, characteristic genital and extragenital responses occur. Estrogens magnify the sexual responses; however, sexual responses may also occur in estrogen-deficient individuals. Sexual dysfunction may be due to organic or functional disturbances. For example, a variety of diseases affecting neurologic function, including diabetes mellitus and multiple sclerosis, may interrupt sexual arousal. More commonly, local pelvic disorders, such as endometriosis and vaginitis, both of which cause dyspareunia (difficult or painful coitus) may also affect a woman's sexual response. In addition, estrogen deficiency, causing vaginal atrophy and dyspareunia, is a common cause of sexual dysfunction. For a discussion of other causes of female sexual dysfunction, see, e.g., Kaplan, *The Evaluation of Sexual Disorders: Psychological and Medical Aspects* (Brunner-Mazel, New York, N.Y. 1983), and Kolodny et al., *Textbook of Sexual Medicine* (Little, Brown & Co., Boston, Mass. 1979).

Excitement stage dysfunction generally involves touch sensation impairment, loss of clitoral sensation, vaginal dryness, and urinary incontinence. Such excitement phase dysfunction generally results in dyspareunia. Dyspareunia is thought to affect approximately 40% of women, due in large part to inadequate lubrication. It has been estimated that over 40 million women will suffer dyspareunia at some time in their lives. On the order of twenty-five million women will experience dyspareunia in the peri- and postmenopausal period (see, Kelly, *Clinical Practice and Sexuality* 8(8):2 (1992) and Sato et al., *Clinical Practices in Sexuality* 8(5):1 (1992)). Contemporary symptomatic treatments generally involve the use of physiologically safe lubricants such as egg white, K-Y surgical lubrication jelly (hydroxyethylcellulose), ASTROGLIDE® (Astro-Lube, Inc., N. Hollywood, Calif.), and REPLENS® (Columbia Laboratories, Inc., Aventura, Fla.). See, e.g., Semmens, *Medical Aspects of Human Sexuality* 8:85–86 (1974); and Frishmen et al., *Fertility and Sterility* 58(3):630 (1992). When symptomatic treatment fails, pharmacological treatment may be indicated.

Estrogen therapy is commonly used in the pharmacological treatment of sexual dysfunction in women. Estrogen-based therapies are generally used to increase mucous production, provide vasodilatory effects, or to increase the general health of the vagina. Nadelson et al. (eds.), *Treatment Interventions in Human Sexuality* (Plenum Press, New York 1983). In such treatments, estrogen is administered orally, parenterally (e.g., by injection), or topically. With oral administration, the estrogen concentration encountered by the liver is generally four- to five-fold greater than estrogen levels in peripheral blood (the "first pass effect"). This effect may lead to an undesirable increase in the production of certain coagulation factors and renin substrates by the liver. Parenterally administered estrogen avoids the first pass effect in the liver. However, all estrogen-based therapies are known to increase the risk of endometrial hyperplasia, endometrial cancer and breast cancer in treated individuals.

Because of the increased risk of endometrial hyperplasia and endometrial cancer encountered with unopposed estrogen therapies, estrogen/progestogen combinations have been employed. However, progestogens are known to have some androgenic activity. Further, common side effects from such therapies include uterine bleeding and the continuation of menstrual periods. Accordingly, there remains a need in the art to provide safer and more ways of treating female sexual dysfunction.

The present invention is directed to the aforementioned need in the art, and provides a new, highly effective method of treating sexual dysfunction in women. The method involves vaginal and/or vulvar administration of a pharmaceutical formulation containing a vasoactive agent, e.g., a prostaglandin, VIP or a VIP agonist or the like.

Drug therapy for treating female sexual dysfunction has been described. For example, U.S. Pat. No. 4,507,323 to Stem describes the use of the anxiolytic m-chloro-α-t-butylamino-propiophenone in the treatment of sexual dysfunction in both male and female individuals. Pharmaceutical compositions containing the agent are described, which are presented in discrete units, e.g., cachets, tablets, capsules, ampules and suppositories, for oral or rectal delivery of the agent.

Additionally, U.S. Pat. No. 4,521,421 to Foreman describes the treatment of sexual dysfunction in male and female individuals using the stereoisomers of octahydropyrimido[4,5-g]quinolines, centrally acting dopamine agonists.

U.S. Pat. No. 5,190,967 to Riley describes the treatment of sexual disorders in male and female individuals using heterocyclic benzodioxinopyrrole compounds, which, like the drugs described in the aforementioned patents, are centrally acting agents.

U.S. Pat. No. 5,565,466 to Gioco et al., U.S. Pat. No. 5,731,339 to Lowrey, and U.S. Pat. No. 5,773,457 to Nahoum pertain to methods for modulating the human sexual response, with the Gioco et al. and Lowrey patents emphasizing the utility of phentolamine as an active agent.

A number of references describe various methods and devices suitable for vaginal or uterine drug administration, and may accordingly be of some interest with respect to the present invention. The following are representative of such references:

U.S. Pat. No. 3,967,618 to Zaffaroni describes an intrauterine device adapted for drug delivery. A number of drugs are mentioned as being suitable for use in conjunction with the device. However, the patent does not mention treatment of sexual dysfunction, nor is application of a drug-containing composition to the clitoris or vulvar region disclosed or suggested. U.S. Pat. No. 3,948,254 to Zaffaroni is a related patent that describes an intrauterine device for continuous administration of a contraceptive agent.

U.S. Pat. No. 4,014,987 to Heller et al. describes a tampon-like device for delivery of a drug to the uterus or vagina. Heller et al. mention that delivery of prostaglandins is a preferred use of the invention; however, there is no disclosure concerning treatment of sexual dysfunction or delivery to the vulvar area.

U.S. Pat. No. 4,564,362 to Burnhill describes a vaginal sponge for controlled release of a contraceptive agent.

U.S. Pat. No. 4,112,942 to Scaife generally describes vaginal administration of medicinal foams.

There are, accordingly, a number of background references relating to treatment of female sexual dysfunction, and cervical or uterine administration of vasoactive agents. However, the present method for treating female sexual dysfunction, by way of vaginal and/or vulvar delivery of a vasoactive agent such as a prostaglandin or VIP or a receptor agonist thereof, is completely novel and unsuggested by the art.

SUMMARY OF THE INVENTION

Accordingly, it is a primary object of the invention to provide a method for treating sexual dysfunction in a female individual by administering a pharmaceutical formulation containing a selected vasoactive agent to the vaginal and/or vulvar area of the individual undergoing treatment.

It is still another object of the invention to provide methods for improving vaginal muscle tone and tissue health, enhancing vaginal lubrication, preventing vaginal atrophy, preventing pain during intercourse as a result of dyspareunia, alleviating vaginal itching and dryness associated with dyspareunia and other conditions, and minimizing collagen misdeposition resulting from hypoxia, each of such methods vaginal and/or vulvar administration of a pharmaceutical formulation containing a selected vasoactive agent, in combination with a pharmaceutically acceptable vehicle.

It is an additional object of the invention to provide such methods wherein the vasoactive agent is vasoactive intestinal polypeptide or an agonist thereof.

It is still an additional object of the invention to provide such methods wherein drug administration is carried out on an as-needed basis.

It is a further object of the invention to provide pharmaceutical formulations useful in conjunction with the aforementioned methods.

Additional objects, advantages, and novel features of the invention will be set forth in part in the description that follows, and in part will become apparent to those skilled in the art upon examination of the following, or may be learned by practice of the invention.

In one aspect of the invention, then, a method is provided for treating sexual dysfunction in a female individual comprising administering to the vagina and/or vulvar area a pharmaceutical formulation containing a selected vasoactive agent. The vasoactive agent is preferably a vasodilator, with preferred vasodilators selected from the group consisting of VIP and vasoactive intestinal polypeptide agonists, both natural and synthetic, and combinations of any of the foregoing. Any number of drug delivery platforms may be used, e.g., suppositories, ointments, creams, gels, solutions and the like, which will be described in detail below. Also, one or more additional types of drugs, i.e., pharmacologically active agents other than vasoactive agents, may be incorporated into the pharmaceutical formulations. In other aspects of the invention, vaginal administration of a vasoactive agent as just described is used to improve vaginal muscle tone and tissue health, to enhance vaginal lubrication, or to minimize collagen misdeposition resulting from hypoxia as well as the associated lack of elasticity resulting from the collagen misdeposition.

In another aspect of the invention, pharmaceutical compositions and dosage forms are provided for carrying out the aforementioned methods. The compositions and dosage forms contain a vasoactive agent as described above, a pharmaceutically acceptable vehicle, and, optionally, one or more additional pharmacologically active agents. The formulations contain a therapeutically effective amount of the active agent, or a therapeutically effective concentration of the active agent, i.e., a concentration that provides a therapeutically effective amount of active agent upon administration of a selected volume of composition.

In another embodiment, packaged kits are provided for individuals to carry out the aforementioned methods. Packaged kits include a pharmaceutical composition or dosage form containing the active agent, a container housing the composition or dosage form during storage and prior to administration, and instructions, e.g., written instructions on a package insert or label, for carrying out drug administration in a therapeutically effective manner. The composition or dosage form may be any of those described herein.

DETAILED DESCRIPTION OF THE INVENTION

Before describing the present invention in detail, it is to be understood that this invention is not limited to delivery of specific drugs, carriers or use of particular drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a vasoactive agent" includes a mixture of two or more vasoactive agents, reference to "a pharmaceutically acceptable excipient" includes mixtures of such excipients, and the like.

In describing and claiming the present invention, the following terminology will be used in accordance with the definitions set out below.

The terms "active agent," "pharmacologically active agent" and "drug" are used interchangeably herein to refer to a chemical compound that induces a desired pharmacological, physiological effect, i.e., in this case, enhancement of female sexual desire and responsiveness. The primary active agents herein are vasoactive intestinal polypeptide and agonists thereof. The terms also encompass pharmaceutically acceptable, pharmacologically active derivatives of those active agents specifically mentioned herein, including, but not limited to, salts, esters, amides, prodrugs, active metabolites, and the like. When the terms "active agent," "pharmacologically active agent" and "drug" are used, then, it is to be understood that applicants intend to include the active agent per se as well as pharmaceutically acceptable, pharmacologically active salts, esters, amides, prodrugs, metabolites, analogs, etc.

The pharmacologically active agents herein are vasoactive intestinal polypeptide and analogs thereof that serve as VIP agonists.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective to enhance female sexual desire and responsiveness.

"Carriers" or "vehicles" as used herein refer to conventional pharmaceutically acceptable carrier materials suitable for drug administration, and include any such materials known in the art that are nontoxic and do not interact with other components of a pharmaceutical composition or drug delivery system in a deleterious manner.

By an "effective" amount or a "therapeutically effective amount" of a drug or pharmacologically active agent is meant a nontoxic but sufficient amount of the drug or agent to provide the desired effect, i.e., treatment of female sexual dysfunction. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" sexual dysfunction, as the term is used herein, encompasses both prevention of sexual dysfunction in clinically asymptomatic individuals and treatment of dysfunction in a clinically symptomatic individual.

By "treating female sexual dysfunction" is meant enhancing female sexual desire and responsiveness. Applicants intend to include the treatment of disorders of female sexual desire and/or response, meaning any disorder or dysfunction that causes a decrease in or absence of female sexual responsiveness or female sexual desire. This includes any persistent or recurrent deficiency in the desire for sexual activity. It also includes decreases in the physiological response to sexual stimulation such as slowed or decreased erectile response of the female erectile tissues; slowed, decreased or absent lubrication of the vagina; slowed, decreased, or absent ability to have orgasms; decreased intensity of or pleasure in orgasms: frigidity; sexual aversion; and disorders of female sexual desire and response that are secondary to a general medical condition such as the menopausal or post-menopausal state, radiotherapy of the pelvis, atherosclerosis, pelvic trauma or surgery, peripheral neuropathies, autonomic neuropathies, diabetes mellitus, and disorders of the innervation of any of the sexual organs. This term also includes substance-induced sexual dysfunction, including but not limited to, decreases in desire and responsiveness secondary to anti-depressants, neuroleptics, anti-hypertensives, tobacco, opiates, alcohol and any other drug found to decrease or eliminate any part of the sexual response cycle. Primary and secondary anorgasmia are included.

By "as-needed" dosing, also referred to as "pro re nata" dosing, "prn" dosing, and "on-demand" dosing or administration, is meant the administration of an active agent at a time just prior to the time at which drug efficacy is wanted, e.g., just prior to anticipated sexual activity, and within a time interval sufficient to provide for the desired therapeutic effect, i.e., enhancement in sexual desire and in sexual responsiveness during sexual activity. "As-needed" administration herein does not involve priming doses or chronic administration, "chronic" meaning administration at regular time intervals on an ongoing basis. As-needed administration may involve administration immediately prior to sexual activity, but will generally be about 0.25 to 72 hours, preferably about 0.5 to 48 hours, more preferably about 1 to 24 hours, most preferably about 1 to 12 hours, and optimally about 1 to 4 hours prior to anticipated sexual activity. "As-needed" administration may or may not involve administration of a sustained release formulation in advance of anticipated sexual activity, with drug release taking place throughout an extended drug delivery period typically in the range of about 4 to 72 hours.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). As discussed therein, immediate and nonimmediate release can be defined kinetically by reference to the following equation:

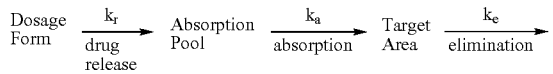

The "absorption pool" represents a solution of the drug administered at a particular absorption site, and $k_r$, $k_a$, and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area. The term "controlled release" as used herein includes any nonimmediate release formulation, including but not limited to sustained release, delayed release, and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period. A sustained release formulation may be administered once to provide a single bolus dose of the active agent, which is then effective for up to a day or even up to several days.

By the term "transdermal" drug delivery is meant delivery by passage of a drug through the skin or mucosal tissue and into the bloodstream.

The term "topical administration" is used in its conventional sense to mean delivery of a topical drug or pharmacologically active agent to the skin or mucosa. Topical administration thus includes transmucosal administration.

Generally, "vaginal delivery" of a pharmaceutical formulation involves administration to the distal several centimeters of the vagina. The terms "vulvar delivery" and "vulvar administration" are used herein to refer to application of a pharmaceutical formulation to the vulvar area of an individual undergoing treatment. The term is intended to encompass application to the clitoris as well as the surrounding vulvar area. The terms "vulvar delivery" and "clitoral delivery" are used interchangeably herein and are both intended to refer to administration to the vulvar area of the individual undergoing treatment.

In order to carry out the method of the invention, VIP or an agonist thereof is administered to the vagina and/or vulvar region of a female individual to enhance sexual desire and responsiveness; the individual may or may not be suffering from a sexual disorder or dysfunction. The active agent is administered locally and transmucosally, i.e., vaginally and/or to the vulvar region.

As used herein, the term "$C_{1-3}$ alkyl" refers to methyl, ethyl, propyl, and isopropyl.

The nomenclature used to define the vasoactive intestinal peptides of the invention is that typically used in the art, wherein the amino group at the N-terminus appears to the left and the carboxyl group at the C-terminus appears to the right. By natural amino acids is meant one of the naturally occurring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. By Nle is meant norleucine. By Orn is meant ornithine. By Ac is meant acetyl ($CH_3CO_2$). Where the amino acid has isomeric forms, it is the L form of the amino acid that is represented unless otherwise expressly indicated.

Analogs of VIP, i.e., those analogs included herein as VIP agonists, are indicated by setting forth the substituted amino acid in brackets before "VIP." Derivatization of the N-terminal amino group is indicated to the left of the bracketed substitutions. Sequence numbers appearing in parentheses to the right of "VIP" indicate amino acid deletions and additions to the native sequence numbering. That is, for example, Ac-[Lys$^{12}$,Nle$^{17}$,Gly$^{29}$]-VIP (2–29) indicates a polypeptide having an amino acid sequence corresponding to native human VIP in which an acetyl group has been substituted for hydrogen at the N-terminus, lysine has been substituted for arginine at position 12 and norleucine has been substituted for methionine at position 17, the histidine at position 1 has been deleted and a glycine has been coupled onto the carboxyl side of asparagine 28, termed position 29. The suffixes "—OH" and "—NH$_2$" following "VIP" refer to the free acid and amide forms of the polypeptide, respectively. In the event neither suffix is used, the expression is intended to encompass both forms.

The following abbreviations are also defined: N—CH$_3$-Ala is N-methyl-alanine, p-F-Phe is fluoro-phenylalanine, 1-Nal is 3-(1'-naphthyl)-alanine, 2-Nal is 3-(2'-naphthyl)-alanine, p-NH$_2$-Phe is p-amino-phenylalanine, O—CH$_3$-Tyr is O-methyl-tyrosine, Cys(Acm) is S-acetoamidomethyl-cysteine, m-F-Tyr is m-fluoro-tyrosine.

In a first embodiment, the invention relates to a method for treating sexual dysfunction in a female individual and involves vaginal and/or vulvar administration of a pharmaceutical formulation containing a vasoactive agent, preferably a vasodilator. Preferred vasodilators are selected from the group consisting of vasoactive intestinal polypeptide, VIP agonists, pharmaceutically acceptable salts, esters, derivatives, prodrugs, and inclusion complexes thereof, and combinations of any of the foregoing, in combination with a pharmaceutically acceptable vehicle.

VIP agonists are, as noted above, useful for practicing the invention. The sequence of human VIP, which is the same as rat, bovine and porcine VIP is known to be:

```
His-Ser-Asp-Ala-Val-Phe-Thr-Asp-Asn-Tyr-Thr-Arg-

Leu-Arg-Lys-Gln-Met-Ala-Val-Lys-Lys-Tyr-Leu-Asn-

Ser-Ile-Leu-Asn.
```

In the conventional single letter amino acid code the VIP amino acid sequence is: H-S-D-A-V-F-T-D-N-Y-T-R-L-R-K-Q-M-A-V-K-K-Y-L-N-S-I-L-N (SEQ. ID. NO.: 1). VIP sequences from other species are known to exhibit homology to human VIP and therefore expected to exhibit VIP agonistic and/or antagonistic activity. Partial agonists of VIP that are also antagonists of VIP, for example agonists that are less active than endogenously secreted VIP may be used in the methods of the invention depending upon activity relative to physiologic human VIP and local dosage. The usefulness of partial VIP agonists for practicing the invention may be ascertained by conventional trials and pharmacologic assays known in the art.

Representative vasoactive intestinal polypeptide analogs include peptides having the following amino acid sequences:

```
[Lys12, Nle17]-VIP;                                    (SEQ. ID. NO.:2)

Ac-[Lys12, Nle17]-VIP;                                 (SEQ. ID. NO.:3)

[Orn12, Nle17]-VIP;                                    (SEQ. ID. NO.:4)

Ac-[Orn12, Nle17]-VIP;                                 (SEQ. ID. NO.:5)

[Ser11, Phe13, Nle17]-VIP;                             (SEQ. ID. NO.:6)

Ac-[Ser11, Phe13, Nle17]-VIP;                          (SEQ. ID. NO.:7)

[Nle17, Thr25]-VIP;                                    (SEQ. ID. NO.:8)

[Nle17, Thr24]-VIP;                                    (SEQ. ID. NO.:9)

[Ala9, Nle17]-VIP;                                     (SEQ. ID. NO.:10)

Ac-[Ala9, Nle17]-VIP;                                  (SEQ. ID. NO.:11)

[Lys14, Nle17]-VIP;                                    (SEQ. ID. NO.:12)

[Nle17, Val26, Thr28]-VIP;                             (SEQ. ID. NO.:13)

[Lys12, Lys14, Nle17, Val26, Thr28]-VIP;               (SEQ. ID. NO.:14)

[Nle17, Thr28]-VIP;                                    (SEQ. ID. NO.:15)

Ac-[Nle17, Thr28]-VIP;                                 (SEQ. ID. NO.:16)

[Lys12, Nle17, Val26, Thr28]-VIP;                      (SEQ. ID. NO.:17)

Ac-[Orn12, Nle17, Val26, Thr28]-VIP;                   (SEQ. ID. NO.:18)

Ac-[Lys12, Lys14, Nle17, Val26, Thr28]-VIP;            (SEQ. ID. NO.:19)

Ac-[Lys12, Nle17, Thr25, Val26, Thr28]-VIP;            (SEQ. ID. NO.:20)

Ac-[Lys12, Nle17, Val26, Ala28]-VIP;                   (SEQ. ID. NO.:21)

Ac-[Lys12, Nle17, Val26, Ala27, Thr28]-VIP;            (SEQ. ID. NO.:22)

Ac-[Lys12, Nle17, Ala26, Thr28]-VIP;                   (SEQ. ID. NO.:23)

Ac-[Lys12, Nle17, Ala25, Val26, Thr28]-VIP;            (SEQ. ID. NO.:24)
```

-continued

Ac-[Lys$^{12}$, Nle$^{17}$, Ala$^{24}$, Val$^{26}$, Thr$^{28}$]-VIP; (SEQ. ID. NO.:25)
Ac-[Lys$^{12}$, Nle$^{17}$, Ala$^{23}$, Val$^{26}$, Thr$^{28}$]-VIP; (SEQ. ID. NO.:26)
Ac-[Lys$^{12}$, Nle$^{17}$, Ala$^{22}$, Val$^{26}$, Thr$^{28}$]-VIP; (SEQ. ID. NO.:27)
Ac-[Lys$^{12}$, Nle$^{17}$, Ala$^{21}$, Val$^{26}$, Thr$^{28}$]-VIP; (SEQ. ID. NO.:28)
Ac-[Lys$^{12}$, Nle$^{17}$, Ala$^{20}$, Val$^{26}$, Thr$^{28}$]-VIP; (SEQ. ID. NO.:29)
Ac-[Lys$^{12}$, Nle$^{17}$, Ala$^{19}$, Val$^{26}$, Thr$^{28}$]-VIP; (SEQ. ID. NO.:30)
Ac-[Lys$^{12}$, Ala$^{17}$, Val$^{26}$, Thr$^{28}$]-VIP; (SEQ. ID. NO.:31)
Ac-[Lys$^{12}$, Ala$^{16}$, Nle$^{17}$, Val$^{26}$, Thr$^{28}$]-VIP; (SEQ. ID. NO.:32)
Ac-[Lys$^{12}$, Ala$^{15}$, Nle$^{17}$, Val$^{26}$, Thr$^{28}$]-VIP; (SEQ. ID. NO.:33)
Ac-[Lys$^{12}$, Ala$^{14}$, Nle$^{17}$, Val$^{26}$, Thr$^{28}$]-VIP; (SEQ. ID. NO.:34)
Ac-[Lys$^{12}$, Ala$^{13}$, Nle$^{17}$, Val$^{26}$, Thr$^{28}$]-VIP; (SEQ. ID. NO.:35)
Ac-[Ala$^{12}$, Nle$^{17}$, Val$^{26}$, Thr$^{28}$]-VIP; (SEQ. ID. NO.:36)
Ac-[Ala$^{11}$, Lys$^{12}$, Nle$^{17}$, Val$^{26}$, Thr$^{28}$]-VIP; (SEQ. ID. NO.:37)
Ac-[Ala$^{10}$, Lys$^{12}$, Nle$^{17}$, Val$^{26}$, Thr$^{28}$]-VIP; (SEQ. ID. NO.:38)
Ac-[Ala$^{9}$, Lys$^{12}$, Nle$^{17}$, Val$^{26}$, Thr$^{28}$]-VIP; (SEQ. ID. NO.:39)
Ac-[Ala$^{8}$, Lys$^{12}$, Nle$^{17}$, Val$^{26}$, Thr$^{28}$]-VIP; (SEQ. ID. NO.:40)
Ac-[Ala$^{7}$, Lys$^{12}$, Nle$^{17}$, Val$^{26}$, Thr$^{28}$]-VIP; (SEQ. ID. NO.:41)
Ac-[Ala$^{6}$, Lys$^{12}$, Nle$^{17}$, Val$^{26}$, Thr$^{28}$]-VIP; (SEQ. ID. NO.:42)
Ac-[Ala$^{5}$, Lys$^{12}$, Nle$^{17}$, Val$^{26}$, Thr$^{28}$]-VIP; (SEQ. ID. NO.:43)
Ac-[Ala$^{3}$, Lys$^{12}$, Nle$^{17}$, Val$^{26}$, Thr$^{28}$]-VIP; (SEQ. ID. NO.:44)
Ac-[Ala$^{2}$, Lys$^{12}$, Nle$^{17}$, Val$^{26}$, Thr$^{28}$]-VIP; (SEQ. ID. NO.:45)
Ac-[Ala$^{1}$, Lys$^{12}$, Nle$^{17}$, Val$^{26}$, Thr$^{28}$]-VIP; (SEQ. ID. NO.:46)
Ac-[Gly$^{1}$, Lys$^{12}$, Nle$^{17}$, Val$^{26}$, Thr$^{28}$]-VIP; (SEQ. ID. NO.:47)
Ac-[Leu$^{5}$, Lys$^{12}$, Nle$^{17}$, Val$^{26}$, Thr$^{28}$]-VIP; (SEQ. ID. NO.:48)
Ac-[1-Nal$^{6}$, Lys$^{12}$, Nle$^{17}$, Val$^{26}$, Thr$^{28}$]-VIP; (SEQ. ID. NO.:49)
Ac-[p-F-Phe$^{6}$, Lys$^{12}$, Nle$^{17}$, Val$^{26}$, Thr$^{28}$]-VIP; (SEQ. ID. NO.:50)
Ac-[Glu$^{8}$, Lys$^{12}$, Nle$^{17}$, Val$^{26}$, Thr$^{28}$]-VIP; (SEQ. ID. NO.:51)
Ac-[2-Nal$^{10}$, Lys$^{12}$, Nle$^{17}$, Val$^{26}$, Thr$^{28}$]-VIP; (SEQ. ID. NO.:52)
Ac-[p-NH$_2$-Phe$^{10}$, Lys$^{12}$, Nle$^{17}$, Val$^{26}$, Thr$^{28}$]-VIP; (SEQ. ID. NO.:53)
Ac-[O-CH$_3$-Tyr$^{10}$, Lys$^{12}$, Nle$^{17}$, Val$^{26}$, Thr$^{28}$]-VIP; (SEQ. ID. NO.:54)
Ac-[Lys$^{12}$, Nle$^{17}$, m-F-Tyr$^{22}$, Val$^{26}$, Thr$^{28}$]-VIP; (SEQ. ID. NO.:55)
Ac-[Lys$^{12}$, Nle$^{17}$, Val$^{26}$, Thr$^{28}$, Gly$^{29,30}$, Met$^{31}$]-VIP; (SEQ. ID. NO.:56)
Ac-[Lys$^{12}$, Nle$^{17}$, Val$^{26}$, Thr$^{28}$, Gly$^{29,30}$, Cys(Acm)$^{31}$]-VIP; (SEQ. ID. NO.:57)
Ac-[Lys$^{12}$, Nle$^{17}$, Val$^{26}$, Thr$^{28}$, Gly$^{29,30}$, Thr$^{31}$]-VIP; (SEQ. ID. NO.:58)
Ac-[Lys$^{12}$, Nle$^{17}$, Val$^{26}$, Thr$^{28}$, Ala$^{29,30}$, Met$^{31}$]-VIP; (SEQ. ID. NO.:59)
Ac-[Lys$^{12}$, Nle$^{17}$, Val$^{26}$, Thr$^{28}$, Ala$^{29-31}$]-VIP; (SEQ. ID. NO.:60)
Ac-[Lys$^{12}$, Nle$^{17}$, Val$^{26}$, Thr$^{28}$, Gly$^{29}$, Lys$^{30}$]-VIP; (SEQ. ID. NO.:61)
Ac-[Lys$^{12}$, 14, Nle$^{17}$, Ala$^{19}$, Val$^{26}$, Thr$^{28}$]-VIP; (SEQ. ID. NO.:62)
Ac-[2-Nal$^{10}$, Lys$^{12}$, Ala$^{17}$, Val$^{26}$, Thr$^{28}$]-VIP; (SEQ. ID. NO.:63)
Ac-[Glu$^{8}$, Lys$^{12}$, Nle$^{17}$, Val$^{26}$, Thr$^{28}$, Ala$^{29,30}$, Met$^{31}$]-VIP; (SEQ. ID. NO.:64)

-continued

| | |
|---|---|
| Ac-[Glu$^8$, Lys$^{12}$, Nle$^{17}$, Val$^{26}$, Thr$^{28}$, Phe$^{31}$]-VIP; | (SEQ. ID. NO.:65) |
| Ac-[p-F-Phe$^6$, Glu$^8$, Lys$^{12}$, Nle$^{17}$, Ala$^{19}$, Val$^{26}$, Thr$^{28}$, Gly$^{29,30}$, Cys(Acm)$^{31}$]-VIP; | (SEQ. ID. NO.:66) |
| Ac-[p-F-Phe$^6$, p-NH$_2$-Phe$^{10}$, Lys$^{12}$, Nle$^{17}$, Val$^{26}$, Thr$^{28}$]-VIP; | (SEQ. ID. NO.:67) |
| Ac-[Lys$^{12}$, Ala$^{17}$, Val$^{26}$, Thr$^{28}$, Gly$^{29,30}$, Cys(Acm)$^{31}$]-VIP; | (SEQ. ID. NO.:68) |
| Ac-[Glu$^8$, Lys$^{12, 14}$, Nle$^{17}$, Val$^{26}$, Thr$^{28}$, Gly$^{29, 30}$, Met$^{31}$]-VIP; | (SEQ. ID. NO.:69) |
| Ac-[p-NH$_2$-Phe$^{10}$, Lys$^{12}$, Nle$^{17}$, Ala$^{19}$, Val$^{26}$, Thr$^{28}$]-VIP; | (SEQ. ID. NO.:70) |
| Ac-[p-F-Phe$^6$, Glu$^8$, Lys$^{12}$, Nle$^{17}$, Val$^{26}$, Thr$^{28}$, Gly$^{29,30}$, Cys(Acm)$^{31}$]-VIP; | (SEQ. ID. NO.:71) |
| Ac-[Glu$^8$, Lys$^{12}$, Ala$^{17, 19}$, Val$^{26}$, Thr$^{28}$, Gly$^{29,30}$, Met$^{31}$]-VIP; | (SEQ. ID. NO.:72) |
| Ac-[Glu$^8$, Lys$^{12}$, Nle$^{17}$, Val$^{26}$, Thr$^{28}$, Gly$^{29,30}$, Ala$^{31}$]-VIP; | (SEQ. ID. NO.:73) |
| Ac-[Glu$^8$, Lys$^{12}$, Nle$^{17}$, Ala$^{19}$, Val$^{26}$, Thr$^{28}$, Gly$^{29,30}$, Met$^{31}$]-VIP; | (SEQ. ID. NO.:74) |
| Ac-[p-F-Phe$^6$, Lys$^{12}$, Nle$^{17}$, Ala$^{19}$, Val$^{26}$, Thr$^{28}$, Gly$^{29,30}$, Cys(Acm)$^{31}$]-VIP; | (SEQ. ID. NO.:75) |
| Ac-[Glu$^8$, Lys$^{12}$, Nle$^{17}$, Val$^{26}$, Thr$^{28}$, Gly$^{29,30}$, Ser$^{31}$]-VIP; | (SEQ. ID. NO.:76) |
| Ac-[p-F-Phe$^6$, Glu$^8$, Lys$^{12}$, Nle$^{17}$, Ala$^{19}$, Val$^{26}$, Thr$^{28}$]-VIP; | (SEQ. ID. NO.:77) |
| Ac-[Glu$^8$, Orn$^{12}$, Nle$^{17}$, Val$^{26}$, Thr$^{28}$]-VIP; | (SEQ. ID. NO.:78) |
| Ac-[Lys$^{12}$, Nle$^{17}$, Ala$^{25}$, Leu$^{26}$, Lys$^{27,28}$, Gly$^{29,30}$, Thr$^{31}$]-VIP; | (SEQ. ID. NO.:79) |
| Ac-[Glu$^8$, Lys$^{12}$, Nle$^{17}$, Val$^{26}$, Thr$^{28}$, Ala$^{29-31}$]-VIP; | (SEQ. ID. NO.:80) |
| Ac-[Lys$^{12}$, Ala$^{17, 19}$, Val$^{26}$, Thr$^{28}$]-VIP; | (SEQ. ID. NO.:81) |
| Ac-[Glu$^8$, Lys$^{12}$, Nle$^{17}$, Val$^{26}$, Thr$^{28}$, Gly$^{29}$, Lys$^{30}$]-VIP; | (SEQ. ID. NO.:82) |
| Ac-[p-HN$_2$-Phe$^{10}$, Lys$^{12}$, Nle$^{17}$, Val$^{26}$, Thr$^{28}$, Gly$^{29,30}$, Cys(Acm)$^{31}$]-VIP; | (SEQ. ID. NO.:83) |
| Ac-[Glu$^8$, Lys$^{12}$, Nle$^{17}$, Val$^{26}$, Thr$^{28}$, Gly$^{29,30}$, Cys(Acm)$^{31}$]-VIP; | (SEQ. ID. NO.:84) |
| Ac-[Glu$^8$, Lys$^{12}$, Nle$^{17}$, Val$^{26}$, Thr$^{28}$, Gly$^{29,30}$, Met$^{31}$]-VIP; | (SEQ. ID. NO.:85) |
| CH$_3$S(CH$_2$)$_2$CO-[Lys$^{12}$, Nle$^{17}$, Val$^{26}$, Thr$^{28}$]-VIP(2-28); | (SEQ. ID. NO.:86) |
| CH$_3$SO(CH$_2$)$_2$CO-[Lys$^{12}$, Nle$^{17}$, Val$^{26}$, Thr$^{28}$]-VIP(2-28); | (SEQ. ID. NO.:87) |
| Ac-[N-CH$_3$-Ala1, Lys$^{12}$, Nle$^{17}$, Val$^{26}$, Thr$^{28}$]-VIP; | (SEQ. ID. NO.:88) |
| Ac-[Leu$^5$, Orn$^{12}$, Ala$^{17, 19}$, Thr$^{25}$, Val$^{26}$, Thr$^{28}$, Gly$^{29,30}$, Cys(Acm)$^{31}$]-VIP; | (SEQ. ID. NO.:89) |
| Ac-[p-F-Phe$^6$, 2-Nal$^{10}$, Lys$^{12}$, Nle$^{17}$, Val$^{26}$, Thr$^{28}$, Gly$^{29,30}$, Met$^{31}$]-VIP; | (SEQ. ID. NO.:90) |
| Ac-[p-F-Phe$^6$, Glu$^8$, Lys$^{12,14}$, Nle$^{17}$, Ala$^{19}$, Val$^{26}$, Thr$^{28}$, Gly$^{29,30}$, Cys(Acm)$^{31}$]-VIP. | (SEQ. ID. NO.:91) |

Particularly common vasoactive intestinal polypeptide analogs known in the art include the following:

| | |
|---|---|
| Ac-[p-F-Phe$^6$, Lys$^{12}$, Nle$^{17}$, Ala$^{19}$, Val$^{26}$, Thr$^{28}$ Gly$^{29,30}$, Cys(Acm)$^{31}$]-VIP; | (SEQ. ID. NO.:92) |
| Ac-[Leu$^5$, Orn$^{12}$, Ala$^{17}$ Thr$^{25}$, Val$^{26}$, Thr$^{28}$ Gly$^{29-30}$, Cys(Acm)$^{31}$]-VIP; | (SEQ. ID. NO.:93) |
| Ac-[p-F-Phe$^6$, Glu$^8$, Lys$^{12}$, Nle$^{17}$, Ala$^{19}$, Val$^{26}$, Thr$^{28}$, Gly$^{29,30}$, Cys(Acm)$^{31}$]-VIP; | (SEQ. ID. NO.:94) |
| Ac-[N-Me-Ala$^1$, Lys$^{12}$, Nle$^{17}$, Val$^{26}$, Thr$^{28}$]-VIP; | (SEQ. ID. NO.:95) |
| Ac-[p-F-Phe$^6$, p-NH$_2$-Phe$^{10}$, Lys$^{12}$, Nle$^{17}$, Val$^{26}$, Thr$^{28}$]-VIP; | (SEQ. ID. NO.:96) |
| Ac-[Glu$^8$, Lys$^{12}$, Nle$^{17}$, Val$^{26}$, Thr$^{28}$, Gly$^{29,30}$, Met$^{31}$]-VIP; | (SEQ. ID. NO.:97) |
| Ac-[p-NH$_2$-Phe$^{10}$, Lys$^{12}$, Nle$^{17}$, Val$^{26}$, Thr$^{28}$]-VIP; | (SEQ. ID. NO.:98) |
| Ac-[Glu$^8$, Lys$^{12}$, Nle$^{17}$, Val$^{26}$, Thr$^{28}$, Gly$^{29,30}$, Cys(Acm)$^{31}$]-VIP. | (SEQ. ID. NO.:99) |

Other VIP analogs known in the art include:

| Analog | Sequence ID |
|---|---|
| [Nle$^{17}$]-VIP; | (SEQ. ID. NO.:100) |
| Ac-[Nle$^{17}$]-VIP; | (SEQ. ID. NO.:101) |
| [Tyr$^6$]-VIP; | (SEQ. ID. NO.:102) |
| [Phe$^{22}$]-VIP; | (SEQ. ID. NO.:103) |
| [Ser$^7$]-VIP; | (SEQ. ID. NO.:104) |
| [Lys$^7$]-VIP; | (SEQ. ID. NO.:105) |
| [Gln$^7$]-VIP; | (SEQ. ID. NO.:106) |
| [Asn$^7$]-VIP; | (SEQ. ID. NO.:107) |
| [Arg$^7$]-VIP; | (SEQ. ID. NO.:108) |
| [Arg$^9$]-VIP; | (SEQ. ID. NO.:109) |
| [Gln$^9$]-VIP: | (SEQ. ID. NO.:110) |
| [Lys$^9$]-VIP; | (SEQ. ID. NO.:111) |
| [Leu$^9$]-VIP; | (SEQ. ID. NO.:112) |
| [Ser$^9$]-VIP; | (SEQ. ID. NO.:113) |
| [Thr$^9$]-VIP; | (SEQ. ID. NO.:114) |
| [Leu$^{11}$]-VIP; | (SEQ. ID. NO.:115) |
| [Lys$^{11}$]-VIP; | (SEQ. ID. NO.:116) |
| [Asn$^{11}$]-VIP; | (SEQ. ID. NO.:117) |
| [Gln$^{11}$]-VIP; | (SEQ. ID. NO.:118) |
| [Arg$^{11}$]-VIP; | (SEQ. ID. NO.:119) |
| [Thr$^{16}$]-VIP; | (SEQ. ID. NO.:120) |
| [Ser$^{16}$]-VIP; | (SEQ. ID. NO.:121) |
| [Leu$^{16}$]-VIP; | (SEQ. ID. NO.:122) |
| [Lys$^{16}$]-VIP; | (SEQ. ID. NO.:123) |
| [Asn$^{16}$]-VIP; | (SEQ. ID. NO.:124) |
| [Arg$^{16}$]-VIP; | (SEQ. ID. NO.:125) |
| [Arg$^{24}$]-VIP; | (SEQ. ID. NO.:126) |
| [Gln$^{24}$]-VIP; | (SEQ. ID. NO.:127) |
| [Lys$^{24}$]-VIP; | (SEQ. ID. NO.:128) |
| [Leu$^{24}$]-VIP; | (SEQ. ID. NO.:129) |
| [Ser$^{24}$]-VIP; | (SEQ. ID. NO.:130) |
| [Ser$^{12}$]-VIP; | (SEQ. ID. NO.:131) |
| [Ser$^{20}$]-VIP; | (SEQ. ID. NO.:132) |
| [Orn$^{20}$]-VIP; | (SEQ. ID. NO.:133) |
| [Arg$^{20}$]-VIP; | (SEQ. ID. NO.:134) |
| [Phe$^{23}$]-VIP; | (SEQ. ID. NO.:135) |
| [Phe$^{26}$]-VIP; | (SEQ. ID. NO.:136) |
| [Tyr$^{13}$]-VIP; | (SEQ. ID. NO.:137) |
| [Tyr$^{23}$]-VIP; | (SEQ. ID. NO.:138) |
| [Tyr$^{26}$]-VIP; | (SEQ. ID. NO.:139) |
| [Leu$^{26}$]-VIP] | (SEQ. ID. NO.:140) |
| [Ile$^{13}$]-VIP; | (SEQ. ID. NO.:141) |
| [Ile$^{23}$]-VIP; | (SEQ. ID. NO.:142) |
| [Val$^{13}$]-VIP; | (SEQ. ID. NO.:143) |
| [Val$^{23}$]-VIP; | (SEQ. ID. NO.:144) |
| [Nle$^{13}$]-VIP; | (SEQ. ID. NO.:145) |
| [Nle$^{23}$]-VIP; | (SEQ. ID. NO.:146) |
| [Nle$^{26}$]-VIP; | (SEQ. ID. NO.:147) |
| [Arg$^{21}$]-VIP; | (SEQ. ID. NO.:148) |
| [Leu$^{14}$]-VIP; | (SEQ. ID. NO.:149) |
| [Leu$^{21}$]-VIP; | (SEQ. ID. NO.:150) |
| [Orn$^{14}$]-VIP; | (SEQ. ID. NO.:151) |
| [Orn$^{21}$]-VIP; | (SEQ. ID. NO.:152) |
| [Nle$^{14}$]-VIP; | (SEQ. ID. NO.:153) |
| [Nle$^{21}$]-VIP; | (SEQ. ID. NO.:154) |
| [Arg$^{15}$]-VIP; | (SEQ. ID. NO.:155) |
| [Ser$^{15}$]-VIP; | (SEQ. ID. NO.:156) |
| [Gln$^{15}$]-VIP; | (SEQ. ID. NO.:157) |
| [Orn$^{15}$]-VIP; | (SEQ. ID. NO.:158) |
| [Met$^{19}$]-VIP; | (SEQ. ID. NO.:159) |
| [Leu$^{17}$]-VIP; | (SEQ. ID. NO.:160) |
| [Leu$^{19}$]-VIP; | (SEQ. ID. NO.:161) |
| [Val$^{17}$]-VIP; | (SEQ. ID. NO.:162) |
| [Lys$^{17}$]-VIP; | (SEQ. ID. NO.:163) |
| [Lys$^{19}$]-VIP; | (SEQ. ID. NO.:164) |
| [Ile$^{17}$]-VIP; | (SEQ. ID. NO.:165) |
| [Ile$^{19}$]-VIP; | (SEQ. ID. NO.:166) |
| [Nle$^{19}$]-VIP; | (SEQ. ID. NO.:167) |
| [Leu$^{18}$]-VIP; | (SEQ. ID. NO.:168) |
| [Asn$^{25}$]-VIP; | (SEQ. ID. NO.:169) |
| [Leu$^{25}$]-VIP; | (SEQ. ID. NO.:170) |
| [Gln$^{25}$]-VIP; | (SEQ. ID. NO.:171) |
| [Val$^{27}$]-VIP; | (SEQ. ID. NO.:172) |
| [Phe$^3$]-VIP; | (SEQ. ID. NO.:173) |
| [Tyr$^3$]-VIP; | (SEQ. ID. NO.:174) |
| [Phe$^7$]-VIP; | (SEQ. ID. NO.:175) |
| [Tyr$^7$]-VIP; | (SEQ. ID. NO.:176) |
| [Phe$^{19}$]-VIP; | (SEQ. ID. NO.:177) |
| [Tyr$^{19}$]-VIP; | (SEQ. ID. NO.:178) |

| | |
|---|---|
| -continued | |
| [Thr⁴]-VIP; | (SEQ. ID. NO.:179) |
| [Ser⁴]-VIP; | (SEQ. ID. NO.:180) |
| [Asn⁴]-VIP; | (SEQ. ID. NO.:181) |
| [Gln⁴]-VIP; | (SEQ. ID. NO.:182) |
| [Thr⁶]-VIP; | (SEQ. ID. NO.:183) |
| [Ser⁶]-VIP; | (SEQ. ID. NO.:184) |
| [Asn⁶]-VIP; | (SEQ. ID. NO.:185) |
| [Gln⁶]-VIP; | (SEQ. ID. NO.:186) |
| [Ala⁶]-VIP; | (SEQ. ID. NO.:187) |
| [Thr⁸]-VIP; | (SEQ. ID. NO.:188) |
| [Ser⁸]-VIP; | (SEQ. ID. NO.:189) |
| [Asn⁸]-VIP; | (SEQ. ID. NO.:190) |
| [Gln⁸]-VIP; | (SEQ. ID. NO.:191) |
| [Ser²⁸]-VIP; | (SEQ. ID. NO.:192) |
| [Gln²⁸]-VIP; | (SEQ. ID. NO.:193) |
| [Gln¹²]-VIP; | (SEQ. ID. NO.:194) |
| [Gln²⁰]-VIP; | (SEQ. ID. NO.:195) |
| [Ser²¹]-VIP; | (SEQ. ID. NO.:196) |
| [Gln²¹]-VIP; | (SEQ. ID. NO.:197) |
| [Met¹³]-VIP; | (SEQ. ID. NO.:198) |
| [Ile¹⁷]-VIP; | (SEQ. ID. NO.:199) |
| [Met²³]-VIP; | (SEQ. ID. NO.:200) |
| [Met²⁶]-VIP. | (SEQ. ID. NO.:201) |

The preceding list of VIP agonists is by way of example rather than limitation, and other known VIP agonists include permutations of the preceding amino acid sequences and lesser-included deviations from the VIP sequence. Permutations include, for example sequences such as [Thr²⁸]-VIP (SEQ. ID. NO.: 202), which is not listed explicitly above but is a lesser-included deviation from the naturally occurring human VIP sequence that is described, for example, in Ac-[Lys¹²,Nle¹⁷,Val²⁶,Ala²⁷,Thr²⁸]-VIP (SEQ. ID. NO.: 22 and Ac-[Lys¹²,Nle¹⁷,Ala²⁶,Thr²⁸]-VIP (SEQ. ID. NO.: 23), as well as a number of other of the above listed VIP analog sequences, for example, SEQ. ID. NO.: 47. Further a permutation of SEQ. ID. NO. 22 and SEQ. ID. NO. 23, is exemplified by Ac-[Lys¹²,Nle¹⁷,Ala²⁶,Ala²⁷,Thr²⁸]-VIP (SEQ. ID. NO.: 203), which substitutes the Ala²⁶ of SEQ. ID. NO.:22 for the Val²⁶ of SEQ. ID. NO.: 22 and is otherwise identical to SEQ. ID. NO.: 22.

Analogs for use with the instant invention are intended that are essentially equivalent to an explicitly disclosed analog, as specified above. An analog is essentially equivalent to one specified above if it has one or more of the biological activities characteristic of human VIP, has the same number of amino acids as the specified analog and, in comparison with the sequence of the specified analog, has at most five amino acid substitutions, all of which would be considered neutral in the art (i.e., acidic for acidic, basic for basic, uncharged polar for uncharged polar, hydrophobic for hydrophobic, and the like). As is widely known: acidic amino acids are Asp, Glu and gamma-carboxyglutamic acid; basic amino acids are Arg, Lys, His and Orn; hydrophobic amino acids are Ala, Ile, Leu, Met, Nor, Phe, Trp, Tyr, Val, t-butylglycine, norvaline, cyclohexylalanine, t-butylalanine, amino-4-phenylbutyric acid, beta-2-thienylalanine, p-bromophenylalanine, p-chlorophenylalanine, p-iodophenylalanine, p-nitrophenylalanine, 3,5-diiodotyrosine, phenylglycine, and naphthylalanine; uncharged polar amino acids are Asn, Gln, Ser, and Thr. Gly can be substituted for an uncharged polar or a hydrophobic amino acid, but substitutions with Gly are often avoided because helical structures may be destabilized thereby. Substitutions with Pro are generally avoided because of a significant effect on secondary structure of inserting a Pro in place of another amino acid. Substitutions with Cys are also generally avoided because of the reactivity of the sulfhydryl group.

Various synthetic VIP analogs, including many of the above, are explicitly listed in U.S. Pat. Nos. 5,235,907, 5,141,924, 4,734,400 and 4,605,641 to Bolin, and in U.S. Pat. Nos. 4,939,224 and 4,835,252 to Musso et al.

Other suitable VIP agonists include conjugates of VIP and long chain fatty acids or fatty amines, such as $CH_3(CH_2)_6$CO-VIP, $CH_3(CH_2)_{16}$CO-VIP, $CH_3(CH_2)_{16}$CO-VIP$_{7-28}$, $CH_3(CH_2)_{16}$CO-VIP$_{16-28}$, VIP-CONH—$CH_2CH_3$, VIP-CONH—$(CH_2)_3CH_3$, and VIP-CONH—$(CH_2)_7CH_3$, the synthesis of which is described in U.S. Pat. No. 5,147,855 to Gozes et al.

Still other suitable VIP agonists are nitrosylated VIP analogs having the structure VIP-Gly-Cys-NO (SEQ. ID NO.: 204), and the related analogs VIP-Gly-Cys-NH$_2$ (SEQ. ID NO.: 205) and VIP-Gly-Cys (SEQ. ID NO.: 206), preparation of which is described in U.S. Pat. No. 5,612,314 to Stamler et al.

VIP analogs known in the art that are useful for practicing the present invention include those compounds listed above and others that exhibit agonistic VIP activity, preferably strong agonistic activity. Also preferred are those analogs that exhibit agonistic activity with a relatively long biological activity, e.g. a relatively long pharmacologic half-life. Methods for determining the agonistic VIP activity and half-life of a given VIP analog are known to those ordinarily skilled in the art. One attribute of a VIP analog that makes it useful for practicing the invention is a resistance to hydrolysis, a property of synthetic VIP analogs that are disclosed in U.S. Pat. No. 4,939,224 to Musso et al. For bronchodilation.

As the practice of the instant invention will often if not typically involve topical delivery of the vasoactive VIP agonists to the female sex organs, absorption of the VIP analog through the epithelium covering the organ or organs to which it is applied is required for the desired pharmacologic effects. The ordinarily skilled artisan in the therapeutic pharmaceutical art will be able to ascertain whether the absorption of a particular VIP analog is sufficient for the desired effects. VIP analogs are expected to be capable of crossing such epithelial barriers, as the peptide is small relative to proteins.

The ability of VIP peptides to cross such epithelial barriers has been demonstrated in the context of administering VIP by inhalation for bronchodilation. Although administration by inhalation has been shown to be more tissue specific and to have fewer side-effects than intravenous administration but appears to be less effective than intravenous administration (Altiere et al., *Pharmacologist* 25:123 (1983); Bundgaard et al., *Eur. J. Respir. Dis.* 64(Suppl. 128):427–429 (1983); Altiere et al., *Chest* 86:153–154 (1984). This observed lower efficacy of VIP in bronchodilation when administered by inhalation, compared with administration intravenously, is thought to be caused by one or a combination of: (1) rapid degradation of VIP by compounds, including proteolytic enzymes, present in the respiratory tract both in the bronchial airways and the passageways leading thereto (Barrowcliffe et al., Thorax 41:88–93 (1986)); or (2) limited absorption of VIP through nasal and pulmonary mucosa, due in part to the size of VIP (about 3300 Daltons)(Effros and Mason, Am. Rev. Resp. Dis. 127:S59–S65 (1982); Altiere et al., supra).

In the context of the present invention, the ability of various VIP analogs that exhibit VIP agonist activity to cross the pertinent epithelial barrier as a naked peptide is expected. Further, those of skill in the art will appreciate that the ability of VIP agonists to cross the epithelial barrier of the female genitalia for use with the instant invention may be enhanced by known techniques, such as packaging in liposomes or the like.

The above representative VIP analogs may be readily synthesized by known conventional techniques for forming a peptide linkage between amino acids. Such conventional procedures include, for example, all solution phase techniques permitting a condensation between the free alpha amino group of an amino acid or residue thereof having its carboxyl group or other reactive groups protected and the free primary carboxyl group of another amino acid or residue thereof having its amino group or other reactive groups protected.

The process for synthesizing the representative compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the active agents of the present invention include for example any solid phase peptide synthesis method. In such a method the synthesis of the active agents can be carried out by sequentially incorporating the desired amino acid residues one at a time into the growing peptide chain according to the general principles of solid phase methods (Merrifield, J. Amer. Chem. Soc. 85:2149–2154 (1963); Barany et al, The Peptides: Analysis, Synthesis and Biology, 2:1–284 (Gross, E. and Meienhofer, J., eds., Academic Press 1980)).

The chemical syntheses of peptides is widely appreciated to require the protection of reactive side chain groups of the various amino acid moieties, in addition to α-amino or α-carboxyl group of the reacted amino acids, with suitable protecting groups which will prevent a chemical reaction from occurring at that site until the protecting group is ultimately removed. Groups requiring such protection include: α-amino, side chain-amino, carboxyl, hydroxyl, side chain amide, guanidine, and imidazole. Methods for protecting both reactive side chain groups and α-amino or α-carboxyl groups are known in the art and enumerated in U.S. Pat. Nos. 5,235,907, 5,141,924, 4,734,400 and 4,605,641 to Bolin. Although the synthetic organic methods described in the preceding publications may be employed to synthesize VIP analogs described above, many may also be expressed in eukaryotic or prokaryotic cells by use of the appropriate expression vector.

Additional pharmacologically active agents may be co-administered along with the primary active agent, i.e., with the VIP or VIP agonist. Such additional active agents are also referred to herein as "secondary" active agents. Preferred secondary agents are vasoactive agents, particularly vasodilators, selected from the group consisting of vasoactive prostaglandins, endothelin-derived relaxation factors, smooth muscle relaxants, leukotriene inhibitors, pharmaceutically acceptable salts, esters, analogs, derivatives, prodrugs, active metabolites, and inclusion complexes thereof, and combinations of any of the foregoing. Other suitable secondary agents include rho kinase inhibitors, melanocortin peptides, endothelin antagonists, growth factors and other peptidyl drugs; selective androgen receptor modulators (SARMs), neuropeptides, amino acids, serotonin agonists, serotonin antagonists, calcium channel blockers, potassium channel openers, potassium channel blockers, dopamine agonists, dopamine antagonists, non-androgenic steroid hormones, and combinations thereof.

Particularly preferred vasoactive agents are vasoactive prostaglandins selected from the group consisting of naturally occurring prostaglandins, semisynthetic prostaglandins, synthetic prostaglandins, and pharmaceutically acceptable, pharmacologically active salts, esters, amides, inclusion complexes prodrugs, metabolites, and analogs thereof. Racemic, optically enriched or purified stereoisomers of any of these compounds are also included. A suitable unit dose of a prostaglandin herein is in the range of approximately 1 to 5000 µg, preferably in the range of approximately 20 to 2000 µg. Preferred prostaglandins include, but are not limited to, the naturally occurring prostaglandins prostaglandin $E_0$ ($PGE_0$, also referred to 13,14-dihydro-$PGE_1$; hereinafter, the abbreviation "PG" is used for "prostaglandin"), $PGE_1$, 19-hydroxy-$PGE_1$, $PGE_2$, 19-hydroxy-$PGE_2$, $PGA_1$, 19-hydroxy-$PGA_1$, $PGA_2$, 19-hydroxy-$PGA_2$, $PGB_1$, 19-hydroxy-$PGB_1$, $PGB_2$, 19-hydroxy-$PGB_2$, $PGB_3$, $PGD_2$, $PGF_{1\alpha}$, $PGF_{2\alpha}$(dinoprost), $PGE_3$, $PGF_{3\alpha}$, $PGI_2$ (prostacyclin), and combinations thereof. $PGE_0$, $PGE_1$, $PGE_2$, and the hydrolyzable lower alkyl esters thereof (e.g., the methyl, ethyl and isopropyl esters) are, however, particularly preferred. Other suitable prostaglandins are exemplified, without limitation, by arboprostil, carbaprostacyclin, carboprost tromethamine, dinoprost tromethamine, dinoprostone, enprostil, iloprost, lipoprost, gemeprost, metenoprost, sulprostone, tiaprost, viprostil (CL 115,347), viprostil methyl ester, 16,16-dimethyl-$\Delta^2$-$PGE_1$ methyl ester, 15-deoxy-16-hydroxy-16-methyl-$PGE_1$ methyl ester (misoprostol), 16,16-dimethyl-$PGE_1$, 11-deoxy-15-methyl-$PGE_1$, 16-methyl-18,18,19,19-tetrahydrocarbacyclin, 16(RS)-15-deoxy-16-hydroxy-16-methyl-$PGE_1$ methyl ester, (+)-4,5-didehydro-16-phenoxy-α-tetranor-$PGE_2$ methyl ester, 11-deoxy-11α,16,16-trimethyl-$PGE_2$, (+)-11α,16α,16β-dihydroxy-1,9-dioxo-1-(hydroxymethyl)-16-methyl-trans-prostene, 9-chloro-16,16-dimethyl-$PGE_2$, 16,16-dimethyl-$PGE_2$, 15(S)-15-methyl-$PGE_2$, 9-deoxy-9-methylene-16,16-dimethyl-$PGE_2$, potassium salt, 19(R)-hydroxy-$PGE_2$, and 11-deoxy-16,16-dimethyl-$PGE_2$.

Additional vasoactive agents useful as secondary active agents herein include endothelin-derived relaxation factors ("EDRFs") such as nitric oxide releasing agents, e.g., sodium nitroprusside and diazenium diolates, or "NONOates." NONOates include, but are not limited to, (Z)-1-{N-methyl-N-[6-(N-methyl-ammoniohexyl)amino]}diazen-1-ium-1,2-diolate ("MAHMA/NO"), (Z)-1-[N-(3-ammoniopropyl)-N-(n-propyl)amino]-diazen-1-ium-1,2-diolate ("PAPA/NO"), (Z)-1-{N-[3-aminopropyl]-N-[4-(3-aminopropylammonio)butyl]amino}diazen-1-ium-1,2-diolate (spermine NONOate or "SPER/NO") and sodium (Z)-1-(N,N-diethylamino)-diazen-1-ium-1,2-diolate (diethylamine NONOate or "DEA/NO") and derivatives thereof). Still other vasoactive agents include vasoactive intestinal polypeptide analogs and derivatives thereof (particularly derivatives in the form of hydrolyzable lower alkyl esters), smooth muscle relaxants, leukotriene inhibitors, calcium channel blockers, β2-adrenergic agonists, angiotensin-converting enzyme ("ACE") inhibitors, angiotensin II receptor antagonists, and phosphodiesterase inhibitors.

Still other suitable vasoactive agents include, but are not limited to: nitrates and like compounds such as nitroglycerin, isosorbide dinitrate, erythrityl tetranitrate, amyl nitrate, molsidomine, linsidomine chlorhydrate ("SIN-1"), S-nitroso-N-acetyl-d,l-penicillamine ("SNAP") and S-nitroso-N-glutathione ("SNO-GLU"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; nimodepine; pinacidil; cyclandelate; dipyridamole; isoxsuprine; chlorpromazine; haloperidol; yohimbine; and trazodone.

Other secondary active agents herein are inhibitors of rho kinase, an enzyme belonging to the rhoA/rho associated kinase pathway, which regulates the state of phosphorylation of myosin phosphatase, in turn leading to the control of smooth muscle contraction. One example of a suitable rho kinase inhibitor has the following structural formula and is identified as Y-27632:

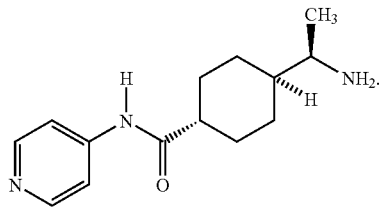

Other suitable rho kinase inhibitors are disclosed, for example, in U.S. Pat. No. 6,218,410.

Additional secondary agents useful herein are peptide analogs of α-melanocyte-stimulating hormone (α-MSH), also referred to as "melanocortin peptides." Such peptides include the sequence His-Phe-Arg-Trp, His-D-Phe-Arg-Trp, or are homologs thereof, and are preferably cyclic. A preferred melanocortin peptide is Ac-Nle-cyclo-(-Asp-His-D-Phe-Arg-Trp-Lys)-OH. See U.S. Pat. No. 6,051,555 to Hadley and International Patent Publication No. WO 01/00224 to Blood et al., assigned to Palatin Technologies, Inc. The aforementioned amino acid residues have their conventional meaning as given in Chapter 2422 of the *Manual of Patent Examining Procedure* (2000). Thus, "Arg" is arginine, "Nle" is norleucine, "His" is histamine, "Phe" is phenylalanine, "D-Phe" is D-phenylalanine, "Trp" is tryptophan, and "Ac" refers to an acetyl moiety, i.e., an acetyl moiety present in a peptide or amino acid sequence that is acetylated.

Suitable endothelin antagonists include antagonists of any or all of the three isoforms of endothelin, i.e., ET-1, ET-2, and ET-3, and are exemplified by: phenoxyphenylacetic acids and derivatives thereof, such as N-(4-isopropylbenzene-sulfonyl)-α-(4-carboxy-2-n-propylphenoxy)-3,4-methylenedioxyphenyl acetamide dipotassium salt, 2-[(2,6-dipropyl-4-hydroxymethyl)-phenoxy]-2-(4-phenoxyphenyl)-acetic acid, 2-[(2,6-dipropyl-4-hydroxymethyl)phenoxy]-2-(4-phenylphenyl)acetic acid, 2-[(2,6-dipropyl-4-hydroxymethyl)phenoxy]-2-(3-carboxyphenyl)-acetic acid, 2-[(2,6-dipropyl-4-hydroxymetyhl) phenoxy]-2-(3,4-ethylenedioxyphenyl)acetic acid, 2-[(2,6-dipropyl-4-hydroxymethyl)phenoxy]-2-(3,4,5-trimethoxyphenyl)acetic acid, 2-[(2,6-dipropyl-4-hydroxymethyl)phenoxy]-2-(3,4-methylenedioxyphenyl) acetic acid, N-(4-dimethylaminobenzenesulfonyl)-2-(4-methoxycarbonyl-2-propylphenoxy)-2-(3,4-methylenedioxyphenyl) acetamide, N-(2-methylbenzenesulfonyl)-2-(4-methoxycarbonyl-2-propylphenoxy)-2-(3,4-methylenedioxyphenyl)acetamide, N-(2-methoxycarbonyl-benzenesulfonyl)-2-(4-methoxycarbonyl-2-propylphenoxy)-2-(3,4-methylenedioxy-phenyl) acetamide, N-(2-chlorobenzene-sulfonyl)-2-(4-methoxycarbonyl-2-propylphenoxy)-2-(3,4-methylenedioxyphenyl) acetamide, and others, as described in U.S. Pat. No. 5,565,485; and certain isooxazoles, oxazoles, thiazoles, isothiazoles and imidazoles, as described, for example, in U.S. Pat. No. 6,136,828. Numerous other endothelin antagonists may be used as secondary agents herein, and will be known to those of ordinary skill in the art and/or are described in the pertinent patents, literature, and texts.

Peptidyl drugs include the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin.

Selective androgen receptor modulators (SARMs) include LGD2226 and/or LGD1331, both available from Ligand Pharmaceuticals (San Diego, Calif.). See Negro-Villar et al. *J. Clin. Endocrinol. & Metabol.* 84(10):3459–62 (1999).

Suitable neuropeptides include bradykinin, kallidin, des-Arg$^9$-bradykinin, des-Arg$^{10}$-kallidin, des-Arg$^9$-[Leu$^8$]-bradykinin, [D-Phe$^7$]-bradykinin, HOE 140, neuropeptide Y, calcitonin gene-related peptide (cGRP), enkaphalins and related opioid peptides such as Met$^5$-enkaphalin, Leu$^5$-enkephalin, α-, β- and γ-endorphin, α- and β-neo-endorphin, and dynorphin, as well as the neurotransmitters GABA (γ-aminobutyric acid), glycine, glutamate, acetylcholine, dopamine, epinephrine, 5-hydroxytryptamine, substance P, serotonin, and catecholamines.

One or more amino acids may be included in the present formulations. As used herein, the term "amino acid" includes the conventional amino acids, e.g., phenylalanine, leucine, isoleucine, methionine, valine, serine, proline, threonine, alanine, tyrosine, histidine, glutamine, asparagine, lysine, aspartic acid, glutamic acid, cysteine, tryptophan, arginine, and glycine, with arginine being particularly preferred. In addition, the term "amino acid" will also include amino acid derivatives, e.g., 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, and nor-leucine, in addition to stereoisomers (e.g., D-amino acids) of the twenty conventional amino acids. Combinations of any of the foregoing are contemplated as well. Preferred amino acids are the neuroactive amino acids y-aminobutyric acid (GABA), glycine, β-alanine, taurine, and glutamate.

Suitable serotonin agonists include, but are not limited to 2-methyl serotonin, buspirone, ipsaperone, tiaspirone, gepirone, ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, trazodone, zacopride, mezacopride, and combinations thereof. Suitable serotonin antagonists include, for example, ondansetron, granisetron, metoclopramide, tropisetron, dolasetron, palonosetron, trimethobenzamide, methysergide, risperidone, ketanserin, ritanserin, clozapine, amitriptyline, MDL 100,907 (R(+)-α-(2,3-dimethoxyphenyl)-1-[2-(4-fluorophenyl)ethyl]-4-piperidine-methanol) (Marion Merrell Dow), azatadine, cyproheptadine, fenclonine, chlorpromazine, mianserin and combinations thereof.

Representative ergot alkaloids include ergotamine and ergotamine analogs, e.g., acetergamine, brazergoline, bromerguride, cianergoline, delorgotrile, dihydroergotamine, disulergine, ergonovine, ergonovine maleate, ergotamine tartrate, etisulergine, lergotrile, lysergide, mesulergine, metergoline, metergotamine, nicergoline, pergolide, propisergide, proterguride and terguride.

Calcium channel blockers that are suitable for use according to the present invention include, without limitation, amlodipine, felodipine, isradipine, nicardipine, nifedipine, nimodipine, nisoldipine, nitrendipine, bepridil, diltiazem, verapamil, and combinations thereof.

Potassium channel openers include, but are not limited to, pinacidil, diazoxide, cromakalim, nicorandil, minoxidil, (N-cyano-N'-(1,1-dimethylpropyl)-N"-3-pyridyl-guanidine (P-1075), and N-cyano-N'-(2-nitroxyethyl)-3-pridinecarboximidamide monomethanesulfonate (KRN 2391).

Potassium channel blockers include tedisamil, agitoxin-2, apamin, BDS-I, BDS-II, charybdotoxin, α-dendrotoxin, β-dendrotoxin, γ-dendrotoxin, δ-dendrotoxin, dendrotoxin-I, dendrotoxin-K, E-4031, iberiotoxin, kaliotoxin, MCD-peptide, margatoxin, noxiustoxin, paxilline, penitrem A, stichodactyla, tertiapin, tityustoxin K alpha, verruculogen, and combinations thereof. Although all of the active agents are available commercially, most of the listed potassium channel blockers are available from Alomone Labs (Jerusalem, Israel).

Suitable dopamine agonists include, for example, levodopa, bromocriptine, pergolide, apomorphine, piribedil, pramipexole, ropinirole, and combinations thereof. Dopamine antagonists include, without limitation, spiroperidol, benperidol, trifluperidol, pimozide, fluphenazine, droperidol, haloperidol, thiothixene, trifluperazine, moperone, prochlorperazine, molindone, thioridazine, clozapine, chlorpromazine, promazine, sulpiride, clebopride, chlorpromazine, spiperone, flupenthixol, and combinations thereof.

Non-androgenic steroids that may be administered as secondary active agents include progestins and estrogens. Suitable estrogens include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Suitable progestins include acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. It is generally desirable to co-administer a progestin along with an estrogen so that the estrogen is not "unopposed." As is well known in the art, estrogen-based therapies are known to increase the risk of endometrial hyperplasia and cancer, as well as the risk of breast cancer, in treated individuals. Co-administration of estrogenic agents with a progestin has been found to decrease the aforementioned risks.

The primary vasoactive agent—i.e., VIP or an agonist thereof—and the additional active agent or agents may be incorporated into a single formulation, or they may be administered separately, either simultaneously or sequentially. In a preferred embodiment, an androgenic agent is administered prior to administration of VIP or a VIP agonist, i.e., the androgenic agent is administered as a pretreatment. In a particularly preferred embodiment, such a method involves administration of an androgenic agent, e.g., via oral or topical (preferably vulvar and/or vaginal) administration, followed by topical (again, preferably vulvar and/or vaginal) administration of VIP or a VIP agonist.

The formulations herein are administered by topical application to the vulvar region and/or by vaginal drug administration. These pharmaceutical formulations will typically contain one or more pharmaceutically acceptable carriers suited to the particular type of formulation, i.e., gel, ointment, suppository, or the like. The vehicles are comprised of materials of naturally occurring or synthetic origin that do not adversely affect the active agent or other components of the formulation. Suitable carriers for use herein include water, silicone, waxes, petroleum jelly, polyethylene glycol, propylene glycol, liposomes, sugars such as mannitol and lactose, and a variety of other materials, again depending, on the specific type of formulation used. As described in Section IV, infra, dosage forms used for administration to the vulvar region and/or vagina may be used to deliver drug on an as-needed, on-demand basis, and/or throughout an extended, sustained release profile.

The formulations may also include a chemical compound to enhance permeation of the active agent through the mucosal tissue, i.e., a "permeation enhancer." Suitable permeation enhancers include those generally useful in conjunction with topical, transdermal or transmucosal drug delivery. Examples of suitable permeation enhancers include the following: sulfoxides such as dimethylsulfoxide (DMSO) and decylmethylsulfoxide ($C_{10}$MSO); ethers such as diethylene glycol monoethyl ether (available commercially as TRANSCUTOL® (Gattefosse S. A., Saint-Priest, France) and diethylene glycol monomethyl ether; surfactants such as sodium laurate, sodium lauryl sulfate, cetyltrimethylammonium bromide, benzalkonium chloride, Poloxamer (231, 182, 184), TWEEN® (20, 40, 60, 80) (ICI Chemicals, Bridgewater, N.J.), and lecithin (U.S. Pat. No. 4,783,450); the 1-substituted azacycloheptan-2-ones, particularly 1-n-dodecylcyclaza-cycloheptan-2-one (available under the trademark AZONE® (Durham Pharmaceuticals, LLC, Durham, N.C.); see U.S. Pat. Nos. 3,989,816, 4,316,893, 4,405,616 and 4,557,934); alcohols such as ethanol, propanol, octanol, decanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. Mixtures of two or more enhancers may also be used.

In some cases, the formulations may include an enzyme inhibitor, i.e., a compound effective to inhibit enzymes present in the vagina or vulvar area that could degrade or metabolize the active agent. That is, inhibitors of enzymes that decrease or eliminate the activity of the active agent may be included in the formulation so as to effectively inhibit the action of those enzymes. Such compounds include, for example, fatty acids, fatty acid esters, and NAD inhibitors.

The formulations may be in the form of an ointment, cream, emulsion, lotion, gel, solid, solution, suspension, foam or liposomal formulation. Alternatively, the formulations may be contained within a vaginal ring (e.g., as disclosed in U.S. Pat. No. 5,188,835 to Lindskoget al., assigned to Kabi Pharmacia AB), or within a tampon, suppository, sponge, pillow, puff, or osmotic pump system; these platforms are useful solely for vaginal delivery.

Ointments are semisolid preparations that are typically based on petrolatum or other petroleum derivatives. The specific ointment base to be used, as will be appreciated by those skilled in the art, is one that will provide for optimum drug delivery. As with other carriers or vehicles, an ointment base should be inert, stable, nonirritating and nonsensitizing. As explained in *Remington: The Science and Practice of Pharmacy*, supra, at pages 1034–1038, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy* for further information.

Lotions are preparations that may be applied without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. It is generally necessary that the insoluble matter in a lotion be finely divided. Lotions will typically contain suspending agents to produce better dispersions as well as compounds useful for localizing the active agent in contact with the skin, e.g., methylcellulose, sodium carboxymethylcellulose, or the like.

Pharmaceutical emulsion formulations are generally formed from a dispersed phase (e.g., a pharmacologically active agent), a dispersion medium, and an emulsifying agent. If desired, emulsion stabilizers can be included in the formulation as well. A number of pharmaceutically useful emulsions are known in the art, including oil-in-water (o/w) formulations, water-in-oil (w/o) formulations and multiple emulsions such as w/o/w or o/w/o formulations. Emulsifying agents suitable for use in such formulations include, but are not limited to, TWEEN® 60 (ICI Chemicals, Bridgewater, N.J.), SPAN® 80 (Adalor Corp., Exton, Pa.), cetostearyl alcohol, myristyl alcohol, glyceryl monostearate, and sodium lauryl sulfate.

Pharmaceutical creams are, as known in the art, viscous liquid or semisolid emulsions, either oil-in-water or water-in-oil. Cream bases are water-washable, and contain an oil phase, an emulsifier, and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic, or amphoteric surfactant.

The above pharmaceutical formulations are formed by dispersing the finely divided or dissolved active agent uniformly throughout the vehicle or base using conventional techniques, typically by a levigating the agent with a small quantity of the base to form a concentrate, which is then diluted geometrically with further base. Alternatively, a mechanical mixer may be used. Creams, lotions and emulsions are formed by way of a two-phase heat system, wherein oil-phase ingredients are combined under heat to provide a liquified, uniform system. The aqueous-phase ingredients are separately combined using heat. The oil and aqueous phases are then added together with constant agitation and allowed to cool. At this point, concentrated agents may be added as a slurry. Volatile or aromatic materials can be added after the emulsion has sufficiently cooled. Preparation of such pharmaceutical formulations is within the general skill of the art.

The active agent can also be incorporated into a gel formulation using known techniques. Two-phase gel systems generally comprise a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents for use herein include synthetic macromolecules (e.g., carbomers, polyvinyl alcohols, and polyoxyethylene-polyoxypropylene copolymers), gums such as tragacanth, as well as sodium alginate, gelatin, methylcellulose, sodium carboxymethylcellulose, methylhydroxyethyl cellulose and hydroxyethyl cellulose. In order to prepare a uniform gel, dispersing agents such as alcohol or glycerin can be added, or the gelling agent can be dispersed by trituration, mechanical mixing or stirring, or combinations thereof.

Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium ("DOTMA") liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline ("DOPC"), dioleoylphosphatidyl glycerol ("DOPG"), dioleoylphoshatidyl ethanolamine ("DOPE"), among others. These materials can also be mixed with DOTMA in appropriate ratios. Methods for making liposomes using these materials are well known in the art.

Vaginal suppositories are typically manufactured with polyethylene glycol (PEG), polyethylene oxide and/or other low melting point or water-soluble polymers including fatty acid esters. Suppositories may also be applied to the vulvar region, in which case these dosage forms, which are solid at ambient temperature, rapidly melts when placed on the clitoris and within the vulvar region.

Typically, compositions and dosage forms for vulvar and/or vaginal administration will contain the active agent in a concentration such that an effective amount of the agent is delivered with a single application. For example, the composition or dosage form will generally contain sufficient active agent such that an effective amount of the agent is delivered by application of about 0.1 g to 1.0 g. Thus, for delivering about 1.0 µg to about 100 mg, preferably about 0.05 mg to about 50 mg, most preferably about 1.0 mg to about 25 mg, of the composition or dosage form will contain the active agent at a concentration in the range of about 1.0 µg/g to about 1.0 g/g, preferably 50 µg/g to about 500 mg/g, most preferably about 1.0 mg/g to about 250 mg/g.

Delivery of an "as-needed" or "on-demand" dose with topical formulations intended for application to the vulvar region, and/or with vaginal suppositories, is effected by using the appropriate carrier and, when necessary, excipients, for the particular active agent. For example, the active agent's affinity to the carrier must be lower than its affinity to the treated body surface. Optimally, the agent will have a relatively high affinity for the mucosal surface to which it is applied, and a relatively low affinity for the particular carrier. As the affinity of the agent for the body surface remains constant (assuming the agent does not change, e.g., hydrolyze, etc., upon contact with the body surface), a suitable carrier for use in the formulations described herein can be determined by routinely testing a series of different carriers containing the active agent and selecting those carriers that provide the greatest flux of the active agent to the intended tissue, e.g., clitoral tissue. Additionally, one or more permeation enhancers and/or detergents may also be present in the formulation to ensure a rate of delivery sufficient for on-demand administration. A combination of these approaches as well as other approaches may be used to effect delivery of an on-demand dose.

Once the initial, on-demand dose is delivered, the drug delivery system, if present, and/or any remaining formulation may be removed or may remain in place, depending on the preferences of the individual. Alternatively, the formulation and optional drug delivery system may be designed to provide both initial "on-demand" release of the active agent, i.e., as a single, bolus dose, as well as sustained release thereafter, e.g., pulsatile, continuous or cyclical drug release. Such systems can include, for example, osmotic release systems that are capable of delivering an initial, on-demand release of the active agent in addition to variable amounts of the agent in a pulsatile manner thereafter.

Other drug delivery platforms capable of providing an initial release of drug followed by a pulsatile, continuous or cyclical agent release profile include those formed from bioerodible polymers, wherein the active agent is dispersed within a polymer matrix that is surrounded by an immediate release coating of the agent. The immediate release coating ensures effective on-demand administration. The polymers forming the matrix are selected such that they bioerode in the presence of moisture, and provide for sustained agent release at readily predictable rates.

More particularly, release of the active agent can be controlled by dissolution (bioerosion) of a polymer using either encapsulated dissolution control or matrix dissolution control. In encapsulated dissolution control, the on-demand dose of the active agent is located within an outer polymeric or wax membrane that dissolves to provide an initial release of the agent. When the encapsulating membrane comprising an initial release of the agent has dissolved, a core containing additional active agent is then available for release and adsorption across the epithelial or mucosal surfaces of the vagina or vulvar area. Bioerodible coating materials may be selected from a variety of natural and synthetic polymers, depending on the agent to be coated and the desired release characteristics. Exemplary coating materials include gelatins, carnauba wax, shellacs, ethylcellulose, cellulose acetate phthalate, or cellulose acetate butyrate. Following the immediate release of the agent, a uniform sustained release of the agent can be attained by compressing a population of particles of the agent with varying membrane thickness (e.g., varying erosion times) into a tablet form for a single administration.

In matrix dissolution control, the active agent is dissolved or dispersed within a matrix of, for example, an erodible wax. The agent is released for adsorption across the epithelial or mucosal surfaces of the vagina or vulvar area as the matrix bioerodes. The rate of agent availability is generally controlled by the rate of penetration of the dissolution media (i.e., vaginal fluids) into the matrix, wherein the rate of penetration is dependent on the porosity of the matrix material. Bioerodible matrix dissolution delivery systems can be prepared by compressing the active agent with a slowly soluble polymer carrier into a tablet or suppository form. There are several methods of preparing drug/wax particles including congealing and aqueous dispersion techniques. In congealing methods, the active agent is combined with a wax material and either spray-congealed, or congealed and then screened. For an aqueous dispersion, the active agent/wax combination is sprayed or placed in water and the resulting particles collected. Matrix dosage formulations can be formed by compaction or compression of a mixture of active agent, polymer and excipients. Of course, the active agent will also be located in an external coating of the matrix formulation to provide for immediate release of the active agent necessary for on-demand administration.

In an alternative embodiment, the pharmaceutical formulation is administered in the form of biodegradable adhesive film or sheet that adheres to the vulvar area. Such drug delivery systems are generally composed of a biodegradable adhesive polymer based on a polyurethane, a poly(lactic acid), a poly(glycolic acid), a poly(ortho ester), a polyanhydride, a polyphosphazene, or a mixture or copolymer thereof. Preferred biodegradable adhesive polymers include polyurethanes and block copolyurethanes containing peptide linkages, simple mixtures of polyurethanes and polylactides, and copolymers of acrylates and mono- or disaccharide residues.

Preferred dosage forms contain a unit dose of active agent, i.e., a single therapeutically effective dose. For creams, ointments, etc., a "unit dose" requires an active agent concentration that provides a unit dose in a specified quantity of the formulation to be applied, as explained supra. The unit dose of any particular active agent will depend, of course, on the active agent, the needs of the patient, and on the mode of administration. Those of ordinary skill in the art of pharmaceutical formulation can readily deduce suitable unit doses for VIP and various VIP agonists, as well as suitable unit doses for other types of active agents that may be incorporated into a dosage form of the invention.

Drug administration is preferably, although not necessarily, on an as-needed basis, in which case chronic drug administration is not involved. With an immediate release dosage form, i.e., a composition or dosage form that is not "controlled release" as defined hereinabove, as-needed administration may involve drug administration immediately prior to sexual activity, but will generally be in the range of about 0.25 to 72 hours, preferably about 0.5 to 48 hours, more preferably about 1 to 24 hours, most preferably about 1 to 12 hours, and optimally about 1 to 4 hours prior to anticipated sexual activity. As will be appreciated by those in the fields of pharmacology and drug delivery, the upper end of the aforementioned ranges will depend on the pharmacokinetics of the particular active agent administered.

With a sustained release dosage form, a single "as-needed" dose can provide therapeutic efficacy over an extended time period in the range of about 4 to 72 hours, typically in the range of about 4 to 48 hours, more typically in the range of about 4 to 24 hours, depending on the formulation. The release period may be varied by the selection and relative quantity of particular sustained release polymers, as discussed supra.

As-needed administration as described herein has several advantages over chronic pharmacologic intervention. First, chronic administration of some agents, in particular steroids, can result in serious medical complications and alter the balance of naturally occurring steroids in the body. Second, patient compliance can be problematic with a regimented dosing scheme. Furthermore, as-needed administration is convenient and doses are taken only in anticipation of sexual activity. Thus, needless expenditure on wasted dosages is avoided, thereby decreasing the treatment's overall expense.

The patient treated may be a woman suffering from some type of sexual dysfunction or disorder, or may possess "normal" sexual desire and/or "normal" sexual responsiveness as those terms are understood defined by clinicians or other experts. For these "normal" women, the present invention offers heightened sexual desire and responsiveness relative to her typical sexual experience. Often, however, the female patient seeking enhanced sexual desire and responsiveness suffers a sexual dysfunction such as a condition, disease, or disorder that affects one of the four stages of the female sexual response: excitement, plateau, orgasm, or resolution. More specifically, the patient may suffer from any one or more of the following:

a decrease in or absence of female sexual responsiveness or female sexual desire;

a persistent or recurrent deficiency or absence of sexual fantasies and desire for sexual activity;

a decrease in the physiological response to sexual stimulation such as, but not limited to, slowed, decreased or absent erectile response of the female erectile tissues; slowed, decrease or absent lubrication of the vagina; slowed decreased or absent ability to reach orgasm, and decreased intensity of or pleasure in orgasms; frigidity; sexual aversion;

a condition, disease or disorder that may result in decreased sexual desire and responsiveness including, but not limited to, the menopausal or post-menopausal state, radiotherapy of the pelvis, multiple sclerosis, atherosclerosis, pelvic trauma or surgery, peripheral neuropathies, autonomic neuropathies, diabetes mellitus, and disorders of the innervation of any of the sexual organs;

substance-induced decreases in sexual desire and responsiveness including, but not limited to, decreases related to the administration of pharmacologic agents such as, but not limited to, anti-depressants, neuroleptics, anti-hypertensives, opiates, alcohol, and any other agent found to decrease or eliminate any part of the sexual response cycle; and primary and secondary anorgasmia.

In addition to enhancing female sexual desire and responsiveness, the method, compositions, and dosage forms of the invention are useful in improving the tissue health of the female genitalia and preventing vaginal atrophy, preventing pain during intercourse as a result of dyspareunia, and alleviating vaginal itching and dryness associated with dyspareunia and other conditions.

In another embodiment, a packaged kit is provided that contains the pharmaceutical formulation to be administered, i.e., a pharmaceutical formulation containing VIP or a VIP agonist for enhancing female sexual desire and responsiveness, a container (e.g., a vial, a bottle, a pouch, an envelope, a can, a tube, an atomizer, an aerosol can, etc.), preferably sealed, for housing the formulation during storage and prior to use, and instructions for carrying out drug administration in a manner effective to enhance sexual desire and responsiveness. The instructions will typically be written instructions on a package insert, a label, and/or on other components of the kit.

Depending on the type of formulation and the intended mode of administration, the kit may also include a device for administering the formulation (e.g., a transdermal delivery device). The administration device may be a dropper, a swab, a stick, or the nozzle or outlet of an atomizer or aerosol can. The formulation may be any suitable formulation as described herein. For example, the formulation may be an oral dosage form containing a unit dosage of the active agent, or a gel or ointment contained within a tube. The kit may contain multiple formulations of different dosages of the same agent. The kit may also contain multiple formulations of different active agents.

The present kits will also typically include means for packaging the individual kit components, i.e., the pharmaceutical dosage forms, the administration device (if included), and the written instructions for use. Such packaging means may take the form of a cardboard or paper box, a plastic or foil pouch, etc.

It is to be understood that while the invention has been described in conjunction with the preferred specific embodiments thereof, that the foregoing description as well as the examples that follow are intended to illustrate and not limit the scope of the invention. Other aspects, advantages, and modifications within the scope of the invention will be apparent to those skilled in the art to which the invention pertains.

All patents, patent applications, patent publications, and non-patent literature references mentioned herein are incorporated by reference in their entireties.

EXAMPLE 1

A cream formulation is prepared for the topical administration of VIP. The cream includes the following components:

| | |
|---|---|
| VIP | 750 mg |
| Beeswax | 2.7 g |
| Carbopol 934 q.s. | 100.0 g |

Mixing is conducted with tile and spatula until a homogeneous cream mixture is obtained having the prostaglandin uniformly dispersed throughout the composition.

EXAMPLE 2

The procedure of Example 1 is repeated except that the following components are used:

| | |
|---|---|
| Stearyl-VIP | 500 mg |
| Polyethylene glycol 400 | 37.5 g |
| 1,2,6-hexanetriol | 20.0 g |
| Polyethylene glycol 4000 q.s. | 100.0 g |

Stearyl-VIP is prepared as described in U.S. Pat. No. 5,147,855 to Gozes et al. A homogenous cream mixture is obtained.

EXAMPLE 3

The procedure of Example 1 is repeated except that the following components are used:

| | |
|---|---|
| Stearyl VIP$_{7-28}$ | 750 mg |
| Polyethylene glycol 400 | 37.0 g |
| Polyethylene glycol 400 monostearate | 26.0 g |
| Polyethylene glycol 4000 q.s. | 100.0 g |

Stearyl-VIP is prepared as described in U.S. Pat. No. 5,147,855 to Gozes et al. A homogenous cream mixture is obtained.

EXAMPLE 4

The procedure of Example 1 is repeated except that the following components are used:

| | |
|---|---|
| VIP-Gly-Cys-NO (SEQ. ID NO.:204) | 750 mg |
| Polyethylene glycol 400 | 47.5 g |
| Cetyl Alcohol | 5.0 g |
| Polyethylene glycol 4000 q.s. | 100.0 g |

VIP-Gly-Cys-NO (SEQ. ID NO.: 204) is prepared as described in U.S. Pat. No. 5,612,314 to Stamler et al. A homogenous cream mixture is obtained.

EXAMPLE 5

The procedure of Example 1 is repeated except that the following components are used:

| | |
|---|---|
| VIP-Gly-Cys-NH$_2$ (SEQ. ID NO.:205) | 750 mg |
| Polyethylene glycol 400 | 47.5 g |
| Cetyl Alcohol | 5.0 g |
| Polyethylene glycol 4000 q.s. | 100.0 g |

VIP-Gly-Cys-NH$_2$ (SEQ. ID NO.: 205) is prepared as described in U.S. Pat. No. 5,612,314 to Stamler et al. A homogenous cream mixture is obtained.

EXAMPLE 6

An ointment formulation is prepared for the topical administration of VIP. The ointment includes the following components:

| | |
|---|---|
| VIP | 750 mg |
| Anhydrous Ianolin | 20.0 g |
| Mineral oil | 25.0 g |
| White Petrolatum q.s. | 100.0 g |

Mixing is conducted with tile and spatula until a homogeneous ointment mixture is obtained having the VIP uniformly dispersed throughout the composition.

EXAMPLE 7

The procedure of Example 5 is repeated except that the following components are used:

| | |
|---|---|
| VIP | 750 mg |
| Diisopropyl Adipate | 19.95 g |
| White Petrolatum, USP q.s. | 100.0 g |

A homogenous ointment mixture is obtained.

In the cream and ointment formulations described in Examples 1–6, optional ingredients can include materials such as antioxidants, viscosity modifiers (e.g., paraffin wax or lanolin wax), and topical absorption rate modifiers.

EXAMPLE 8

A vaginal suppository formulation is prepared using a synthetic or semisynthetic prostaglandin. The suppository includes the following components:

| | |
|---|---|
| Prostaglandin | 0.25 gm |
| Polyethylene glycol 400 | 37.0 gm |
| Glycerol gelatin | 20.0 gm |
| Polyethylene glycol 4000 q.s. | 100.0 gm |

The polyethylene glycol 400 solution containing prostaglandin is mixed well with glycerol gelatin or similar suppository base such as macrogol, WITEPSOL® (Chemische Werke Witten GmbH, Witten, Germany), or the like, with a mechanical mixing apparatus, and the mixture is then cooled in a suppository mold.

EXAMPLE 9

Suppositories suitable for vaginal administration of a unit dosage of VIP are made as follows. Twenty mg VIP are mixing the selected prostaglandin with 250 mg polyethylene glycol, molecular weight ($M_W$) approximately 4000, and the mixture is heated to a temperature just high enough to produce a melt. The melted mixture is then poured into a mold suitable to provide a suppository, and allowed to cool. The suppository so provided is a unit dosage form suitable for vaginal administration.

EXAMPLE 10

Individuals are assessed and pre-screened to assemble an experimental group of subjects suffering from sexual dysfunction. The compositions prepared in Examples 1–9, formulated with VIP or an analog thereof, are each assessed in the experimental subjects for their ability to increase uterine or vaginal epithelial blood flow. The formulations are applied vaginally and to the vulvar region, and changes in blood flow and/or vaginal fluid production after application of the vasodilating formulations are determined using known methods. Increase in vaginal epithelial blood flow is determined using indirect methods such as photoplethysmography (Levin, *Clinics in Obstet. Gynaecol.* 7:213–252 (1980)), heated oxygen electrode (Wagner et al., "Vaginal Fluid" in *The Human Vagina*, Evans et al. eds. (Amsterdam: Elsevier/North Holland Biomedical Press, pp. 121–137 (1978)), and direct clearance of radioactive Xenon (Wagner et al., *Obstet. Gynaecol.* 56:621–624 (1980)). Changes in vulvar blood flow are monitored using laser Doppler velocimetry (Sarrel, P. M., *Obstet. Gynaecol.* 75:26S–32S (1990)).

Decreased vaginal dryness and/or dyspareunia are negatively correlated with vaginal blood flow rates, wherein increased blood flow to the vagina correlates with increased lubrication and decreased frequency and severity of dyspareunia (Sarrel, P. M., *Obstet. Gynaecol.* 75:26S–32S (1990)). Accordingly, vulvar blood flow after treatment is assessed using laser Doppler velocimetry and compared to baseline levels. Increased vaginal lubrication as a result of treatment with the vasoactive formulations can also be assessed using the methods of Semmens et al., *J. Am. Med. Assoc.* 248:445–448 (1982). The compositions of Examples 1–9, when assessed using such methods, are found to substantially increase blood flow to the vagina and vulvar area and alleviate vaginal dryness.

We claim:

1. A method for treating sexual dysfunction in a female individual caused by lack of increased blood flow in the female individual's genitalia in response to sexual stimulation, comprising administering to the vagina and/or vulvar region of the individual a pharmaceutical formulation that comprises an amount of a vasoactive intestinal polypeptide (VIP) agonist sufficient to cause increased blood flow in the female individual's genitalia, wherein the vasoactive intestinal polypeptide agonist is selected from SEQ ID NOs: 204–206.

2. The method of claim 1, wherein the pharmaceutical formulation further includes a pharmaceutically acceptable carrier suited to vaginal and/or vulvar drug administration.

3. The method of claim 1, further including administering a steroid to the vagina and/or vulvar region of the individual.

4. The method of claim 3, wherein the steroid is selected from the group consisting of progestins, estrogens, androgens, and combinations thereof.

5. The method of claim 1, wherein the pharmaceutical formulation further includes a compound selected from the group consisting of steroid agonists, partial agonists, and antagonists.

6. The method of claim 1, wherein the pharmaceutical formulation is contained within a delivery system selected to provide a predetermined agent release profile.

7. The method of claim 6, wherein the agent release profile is pulsatile.

8. The method of claim 6, wherein the agent release profile is continuous.

9. The method of claim 6, wherein the agent release profile is cyclical.

10. The method of claim 6, wherein the agent release profile is diurnal.

11. The method of claim 1, wherein the pharmaceutical formulation is administered vaginally.

12. The method of claim 11, wherein the pharmaceutical formulation is in the form of an ointment, cream, gel, solid, solution, suspension, foam, or liposomal composition.

13. The method of claim 11, wherein the pharmaceutical formulation is contained within a vaginal ring, tampon, suppository, sponge, pillow, puff, or osmotic pump system.

14. The method of claim 1, wherein the pharmaceutical formulation is administered to the vulvar region.

15. The method of claim 1, wherein the VIP agonist comprises a polypeptide sequence comprising a human vasoactive intestinal polypeptide sequence having amino acid substitutions at one or more positions.

16. The method of claim 15, wherein the vasoactive intestinal polypeptide agonist is terminally modified.

17. The method of claim 4, wherein the steroid is an androgenic agent.

18. The method of claim 17, wherein the androgenic agent is selected from the group consisting of androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone, sodium dehydroepiandrosterone sulfate, 4-dihydrotestosterone, dromostanolone, dromostanolone propionate, ethylestrenol, fluoxymesterone, methyltestosterone, nandrolone phenpropionate, nandrolone decanoate, nandrolone furylpropionate, nandrolone cyclohexane-propionate, nandrolone benzoate, nandrolone cyclohexanecarboxylate, oxandrolone, oxymetholone, stanozolol, testolactone, testosterone, and pharmaceutically acceptable esters of testosterone and 4-dihydrotestosterone.

19. The method of claim 17, wherein the androgenic agent is selected from the group consisting of testosterone, C-17 esters of testosterone, 4-dihydrotestosterone, C-17 esters of 4-dihydrotestosterone, dehydroepiandrosterone, and methyltestosterone.

20. A method for maintaining the health of healthy tissue, or improving the health of unhealthy tissue of the female genitalia, comprising administering to a female individual, on an as-needed basis, a therapeutically effective amount of a vasoactive intestinal polypeptide agonist selected from SEQ ID NOs: 204–206.

21. A method for decreasing vaginal atrophy, comprising administering to a female individual, on an as-needed basis, a therapeutically effective amount of a vasoactive intestinal polypeptide agonist selected from SEQ ID NOs: 204–206.

22. A method for decreasing vaginal pain caused by dyspareunia during sexual intercourse, comprising administering to a female individual suffering from dyspareunia a therapeutically effective amount of a vasoactive intestinal polypeptide agonist selected from SEQ ID NOs: 204–206.

23. A method for alleviating vaginal itching and dryness, comprising administering to a female individual in need of such treatment a therapeutically effective amount of a vasoactive intestinal polypeptide agonist selected from SEQ ID NOs: 204–206 on an as-needed basis.

* * * * *

SEQUENCE LISTING

```
<160> NUMBER OF SEQ ID NOS: 207

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 2
```

```
His Ser Asp Ala Val Phe Thr Asp Asn Tyr Thr Lys Leu Arg Lys Gln
 1               5                  10                  15

Xaa Ala Val Lys Lys Tyr Leu Asn Ser Ile Leu Asn
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 3

His Ser Asp Ala Val Phe Thr Asp Asn Tyr Thr Lys Leu Arg Lys Gln
 1               5                  10                  15

Xaa Ala Val Lys Lys Tyr Leu Asn Ser Ile Leu Asn
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (17)
<223> OTHER INFORMATION: Nle

<400> SEQUENCE: 4

His Ser Asp Ala Val Phe Thr Asp Asn Tyr Thr Xaa Leu Arg Lys Gln
 1               5                  10                  15

Xaa Ala Val Lys Lys Tyr Leu Asn Ser Ile Leu Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (17)
<223> OTHER INFORMATION: Nle

<400> SEQUENCE: 5

His Ser Asp Ala Val Phe Thr Asp Asn Tyr Thr Xaa Leu Arg Lys Gln
 1               5                  10                  15

Xaa Ala Val Lys Lys Tyr Leu Asn Ser Ile Leu Asn
            20                  25
```

```
<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 6

His Ser Asp Ala Val Phe Thr Asp Asn Tyr Ser Arg Phe Arg Lys Gln
 1               5                  10                  15

Xaa Ala Val Lys Lys Tyr Leu Asn Ser Ile Leu Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 7

His Ser Asp Ala Val Phe Thr Asp Asn Tyr Ser Arg Phe Arg Lys Gln
 1               5                  10                  15

Xaa Ala Val Lys Lys Tyr Leu Asn Ser Ile Leu Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 8

His Ser Asp Ala Val Phe Thr Asp Asn Tyr Thr Arg Leu Arg Lys Gln
 1               5                  10                  15

Xaa Ala Val Lys Lys Tyr Leu Asn Thr Ile Leu Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 9

His Ser Asp Ala Val Phe Thr Asp Asn Tyr Thr Arg Leu Arg Lys Gln
 1               5                  10                  15
```

```
Xaa Ala Val Lys Lys Tyr Leu Thr Ser Ile Leu Asn
            20                  25
```

```
<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 10

His Ser Asp Ala Val Phe Thr Asp Ala Tyr Thr Arg Leu Arg Lys Gln
  1               5                  10                  15

Xaa Ala Val Lys Lys Tyr Leu Asn Ser Ile Leu Asn
            20                  25
```

```
<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 11

His Ser Asp Ala Val Phe Thr Asp Ala Tyr Thr Arg Leu Arg Lys Gln
  1               5                  10                  15

Xaa Ala Val Lys Lys Tyr Leu Asn Ser Ile Leu Asn
            20                  25
```

```
<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 12

His Ser Asp Ala Val Phe Thr Asp Asn Tyr Thr Arg Leu Lys Lys Gln
  1               5                  10                  15

Xaa Ala Val Lys Lys Tyr Leu Asn Ser Ile Leu Asn
            20                  25
```

```
<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
```

```
<400> SEQUENCE: 13

His Ser Asp Ala Val Phe Thr Asp Asn Tyr Thr Arg Leu Arg Lys Gln
 1               5                  10                  15

Xaa Ala Val Lys Lys Tyr Leu Asn Ser Val Leu Thr
            20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 14

His Ser Asp Ala Val Phe Thr Asp Asn Tyr Thr Lys Leu Lys Lys Gln
 1               5                  10                  15

Xaa Ala Val Lys Lys Tyr Leu Asn Ser Val Leu Thr
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 15

His Ser Asp Ala Val Phe Thr Asp Asn Tyr Thr Arg Leu Arg Lys Gln
 1               5                  10                  15

Xaa Ala Val Lys Lys Tyr Leu Asn Ser Ile Leu Thr
            20                  25

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 16

His Ser Asp Ala Val Phe Thr Asp Asn Tyr Thr Arg Leu Arg Lys Gln
 1               5                  10                  15

Xaa Ala Val Lys Lys Tyr Leu Asn Ser Ile Leu Thr
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
```

```
        VIP analog
<220> FEATURE:
<221> NAME/KEY: MOD_RES
<222> LOCATION: (17)
<223> OTHER INFORMATION: Nle

<400> SEQUENCE: 17

His Ser Asp Ala Val Phe Thr Asp Asn Tyr Thr Lys Leu Arg Lys Gln
  1               5                  10                  15

Xaa Ala Val Lys Lys Tyr Leu Asn Ser Val Leu Thr
             20                  25

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (17)
<223> OTHER INFORMATION: Nle

<400> SEQUENCE: 18

His Ser Asp Ala Val Phe Thr Asp Asn Tyr Thr Xaa Leu Arg Lys Gln
  1               5                  10                  15

Xaa Ala Val Lys Lys Tyr Leu Asn Ser Val Leu Thr
             20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 19

His Ser Asp Ala Val Phe Thr Asp Asn Tyr Thr Lys Leu Lys Lys Gln
  1               5                  10                  15

Xaa Ala Val Lys Lys Tyr Leu Asn Ser Val Leu Thr
             20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 20

His Ser Asp Ala Val Phe Thr Asp Asn Tyr Thr Lys Leu Arg Lys Gln
  1               5                  10                  15

Xaa Ala Val Lys Lys Tyr Leu Asn Thr Val Leu Thr
```

-continued

```
<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 21

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Ala Thr
            20                  25

<210> SEQ ID NO 22
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 22

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 23

His Ser Asp Ala Val Phe Thr Asp Asn Tyr Thr Lys Leu Arg Lys Gln
 1               5                  10                  15

Xaa Ala Val Lys Lys Tyr Leu Asn Ala Val Leu Thr
            20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 24
```

His Ser Asp Ala Val Phe Thr Asp Asn Tyr Thr Lys Leu Arg Lys Gln
1               5                   10                  15

Xaa Ala Val Lys Lys Tyr Leu Ala Ser Val Leu Thr
            20                  25

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 25

His Ser Asp Ala Val Phe Thr Asp Asn Tyr Thr Lys Leu Arg Lys Gln
1               5                   10                  15

Xaa Ala Val Lys Lys Tyr Ala Asn Ser Val Leu Thr
            20                  25

<210> SEQ ID NO 26
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 26

His Ser Asp Ala Val Phe Thr Asp Asn Tyr Thr Lys Leu Arg Lys Gln
1               5                   10                  15

Xaa Ala Val Lys Lys Ala Leu Asn Ser Val Leu Thr
            20                  25

<210> SEQ ID NO 27
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 27

His Ser Asp Ala Val Phe Thr Asp Asn Tyr Thr Lys Leu Arg Lys Gln
1               5                   10                  15

Xaa Ala Val Lys Ala Tyr Leu Asn Ser Val Leu Thr
            20                  25

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:

```
<221> NAME/KEY: MOD_RES
<222> LOCATION: (17)
<223> OTHER INFORMATION: Nle

<400> SEQUENCE: 28

His Ser Asp Ala Val Phe Thr Asp Asn Tyr Thr Lys Leu Arg Lys Gln
 1               5                  10                  15

Xaa Ala Val Ala Lys Tyr Leu Asn Ser Val Leu Thr
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 29

His Ser Asp Ala Val Phe Thr Asp Asn Tyr Thr Lys Leu Arg Lys Gln
 1               5                  10                  15

Xaa Ala Ala Lys Lys Tyr Leu Asn Ser Val Leu Thr
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 30

His Ser Asp Ala Val Phe Thr Asp Asn Tyr Thr Lys Leu Arg Lys Gln
 1               5                  10                  15

Ala Ala Val Lys Lys Tyr Leu Asn Ser Val Leu Thr
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 31

His Ser Asp Ala Val Phe Thr Asp Asn Tyr Thr Lys Leu Arg Lys Ala
 1               5                  10                  15

Xaa Ala Val Lys Lys Tyr Leu Asn Ser Val Leu Thr
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
```

```
<220> FEATURE:
<221> NAME/KEY: MOD_RES
<222> LOCATION: (17)
<223> OTHER INFORMATION: Nle

<400> SEQUENCE: 32

His Ser Asp Ala Val Phe Thr Asp Asn Tyr Thr Lys Leu Arg Ala Gln
  1               5                  10                  15

Xaa Ala Val Lys Lys Tyr Leu Asn Ser Val Leu Thr
            20                  25

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 33

His Ser Asp Ala Val Phe Thr Asp Asn Tyr Thr Lys Leu Ala Lys Gln
  1               5                  10                  15

Xaa Ala Val Lys Lys Tyr Leu Asn Ser Val Leu Thr
            20                  25

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 34

His Ser Asp Ala Val Phe Thr Asp Asn Tyr Thr Lys Ala Arg Lys Gln
  1               5                  10                  15

Xaa Ala Val Lys Lys Tyr Leu Asn Ser Val Leu Thr
            20                  25

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 35

His Ser Asp Ala Val Phe Thr Asp Asn Tyr Thr Ala Leu Arg Lys Gln
  1               5                  10                  15

Xaa Ala Val Lys Lys Tyr Leu Asn Ser Val Leu Thr
            20                  25

<210> SEQ ID NO 36
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 36

His Ser Asp Ala Val Phe Thr Asp Asn Tyr Ala Lys Leu Arg Lys Gln
 1               5                  10                  15

Xaa Ala Val Lys Lys Tyr Leu Asn Ser Val Leu Thr
            20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 37

His Ser Asp Ala Val Phe Thr Asp Asn Ala Thr Lys Leu Arg Lys Gln
 1               5                  10                  15

Xaa Ala Val Lys Lys Tyr Leu Asn Ser Val Leu Thr
            20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 38

His Ser Asp Ala Val Phe Thr Asp Ala Tyr Thr Lys Leu Arg Lys Gln
 1               5                  10                  15

Xaa Ala Val Lys Lys Tyr Leu Asn Ser Val Leu Thr
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 39

His Ser Asp Ala Val Phe Thr Ala Asn Tyr Thr Lys Leu Arg Lys Gln
 1               5                  10                  15

Xaa Ala Val Lys Lys Tyr Leu Asn Ser Val Leu Thr
```

-continued

```
                20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 40

His Ser Asp Ala Val Phe Ala Asp Asn Tyr Thr Lys Leu Arg Lys Gln
 1               5                  10                  15

Xaa Ala Val Lys Lys Tyr Leu Asn Ser Val Leu Thr
                20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 41

His Ser Asp Ala Val Ala Thr Asp Asn Tyr Thr Lys Leu Arg Lys Gln
 1               5                  10                  15

Xaa Ala Val Lys Lys Tyr Leu Asn Ser Val Leu Thr
                20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 42

His Ser Asp Ala Ala Phe Thr Asp Asn Tyr Thr Lys Leu Arg Lys Gln
 1               5                  10                  15

Xaa Ala Val Lys Lys Tyr Leu Asn Ser Val Leu Thr
                20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 43
```

His Ser Ala Ala Val Phe Thr Asp Asn Tyr Thr Lys Leu Arg Lys Gln
 1               5                  10                 15

Xaa Ala Val Lys Lys Tyr Leu Asn Ser Val Leu Thr
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 44

His Ala Asp Ala Val Phe Thr Asp Asn Tyr Thr Lys Leu Arg Lys Gln
 1               5                  10                 15

Xaa Ala Val Lys Lys Tyr Leu Asn Ser Val Leu Thr
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 45

Ala Ser Asp Ala Val Phe Thr Asp Asn Tyr Thr Lys Leu Arg Lys Gln
 1               5                  10                 15

Xaa Ala Val Lys Lys Tyr Leu Asn Ser Val Leu Thr
            20                  25

<210> SEQ ID NO 46
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 46

Gly Ser Asp Ala Val Phe Thr Asp Asn Tyr Thr Lys Leu Arg Lys Gln
 1               5                  10                 15

Xaa Ala Val Lys Lys Tyr Leu Asn Ser Val Leu Thr
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:

```
<221> NAME/KEY: MOD_RES
<222> LOCATION: (17)
<223> OTHER INFORMATION: Nle

<400> SEQUENCE: 47

His Ser Asp Ala Leu Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: 1-Nal
<220> FEATURE:
<221> NAME/KEY: MOD_RES
<222> LOCATION: (17)
<223> OTHER INFORMATION: Nle

<400> SEQUENCE: 48

His Ser Asp Ala Val Xaa Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 49
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle

<400> SEQUENCE: 49

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 50

His Ser Asp Ala Val Phe Thr Glu Asn Tyr Thr Lys Leu Arg Lys Gln
 1               5                  10                  15
```

```
Xaa Ala Val Lys Lys Tyr Leu Asn Ser Val Leu Thr
            20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: 2-Nal
<220> FEATURE:
<221> NAME/KEY: MOD_RES
<222> LOCATION: (17)
<223> OTHER INFORMATION: Nle

<400> SEQUENCE: 51

His Ser Asp Ala Val Phe Thr Asp Asn Xaa Thr Lys Leu Arg Lys Gln
 1               5                  10                  15

Xaa Ala Val Lys Lys Tyr Leu Asn Ser Val Leu Thr
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: p-NH2-Phe
<220> FEATURE:
<221> NAME/KEY: MOD_RES
<222> LOCATION: (17)
<223> OTHER INFORMATION: Nle

<400> SEQUENCE: 52

His Ser Asp Ala Val Phe Thr Asp Asn Phe Thr Lys Leu Arg Lys Gln
 1               5                  10                  15

Xaa Ala Val Lys Lys Tyr Leu Asn Ser Val Leu Thr
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: O-CH3-Tyr
<220> FEATURE:
<221> NAME/KEY: MOD_RES
<222> LOCATION: (17)
<223> OTHER INFORMATION: Nle

<400> SEQUENCE: 53

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25
```

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (22)
<223> OTHER INFORMATION: m-F-Tyr

<400> SEQUENCE: 54

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 55

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr Gly Gly Met
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 56

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr Gly Gly Cys
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog

```
<220> FEATURE:
<221> NAME/KEY: MOD_RES
<222> LOCATION: (17)
<223> OTHER INFORMATION: Nle

<400> SEQUENCE: 57

His Ser Asp Ala Val Phe Thr Asp Asn Tyr Thr Lys Leu Arg Lys Gln
  1               5                  10                  15

Xaa Ala Val Lys Lys Tyr Leu Asn Ser Val Leu Thr Gly Gly Thr
             20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 58

His Ser Asp Ala Val Phe Thr Asp Asn Tyr Thr Lys Leu Arg Lys Gln
  1               5                  10                  15

Xaa Ala Val Lys Lys Tyr Leu Asn Ser Val Leu Thr Ala Ala Met
             20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 59

His Ser Asp Ala Val Phe Thr Asp Asn Tyr Thr Lys Leu Arg Lys Gln
  1               5                  10                  15

Xaa Ala Val Lys Lys Tyr Leu Asn Ser Val Leu Thr Ala Ala Ala
             20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 60

His Ser Asp Ala Val Phe Thr Asp Asn Tyr Thr Lys Leu Arg Lys Gln
  1               5                  10                  15

Xaa Ala Val Lys Lys Tyr Leu Asn Ser Val Leu Thr Gly Lys
             20                  25                  30

<210> SEQ ID NO 61
<211> LENGTH: 28
```

-continued

```
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 61

His Ser Asp Ala Val Phe Thr Asp Asn Tyr Thr Lys Leu Arg Lys Gln
 1               5                  10                  15

Xaa Ala Ala Lys Lys Tyr Leu Asn Ser Val Leu Thr
             20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: 2-Nal

<400> SEQUENCE: 62

His Ser Asp Ala Val Phe Thr Asp Asn Xaa Thr Lys Leu Arg Lys Gln
 1               5                  10                  15

Ala Ala Val Lys Lys Tyr Leu Asn Ser Val Leu Thr
             20                  25

<210> SEQ ID NO 63
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 63

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Ala Ala Met
             20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (29)
<223> OTHER INFORMATION: Unknown amino acid
<220> FEATURE:
<221> NAME/KEY: MOD_RES
<222> LOCATION: (30)
```

<223> OTHER INFORMATION: Unknown amino acid

<400> SEQUENCE: 64

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Xaa Xaa Phe
             20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 65

His Ser Asp Ala Val Phe Thr Glu Asn Tyr Thr Lys Leu Arg Lys Gln
 1               5                  10                  15

Xaa Ala Ala Lys Lys Tyr Leu Asn Ser Val Leu Thr Gly Gly Cys
             20                  25                  30

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (10)
<223> OTHER INFORMATION: p=NH2-Phe
<220> FEATURE:
<221> NAME/KEY: MOD_RES
<222> LOCATION: (17)
<223> OTHER INFORMATION: Nle

<400> SEQUENCE: 66

His Ser Asp Ala Val Phe Thr Asp Asn Phe Thr Lys Leu Arg Lys Gln
 1               5                  10                  15

Xaa Ala Val Lys Lys Tyr Leu Asn Ser Val Leu Thr
             20                  25

<210> SEQ ID NO 67
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (31)

<223> OTHER INFORMATION: Cys(Acm)

<400> SEQUENCE: 67

His Ser Asp Ala Val Phe Thr Asp Asn Tyr Thr Lys Leu Arg Lys Gln
 1               5                  10                  15

Ala Ala Val Lys Lys Tyr Leu Asn Ser Val Leu Thr Gly Gly Cys
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 68

His Ser Asp Ala Val Phe Thr Glu Asn Tyr Thr Lys Leu Lys Lys Gln
 1               5                  10                  15

Xaa Ala Val Lys Lys Tyr Leu Asn Ser Val Leu Thr Gly Gly Met
            20                  25                  30

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: p-NH2-Phe
<220> FEATURE:
<221> NAME/KEY: MOD_RES
<222> LOCATION: (17)
<223> OTHER INFORMATION: Nle

<400> SEQUENCE: 69

His Ser Asp Ala Val Phe Thr Asp Asn Phe Thr Lys Leu Arg Lys Gln
 1               5                  10                  15

Xaa Ala Ala Lys Lys Tyr Leu Asn Ser Val Leu Thr
            20                  25

<210> SEQ ID NO 70
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 70

```
His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Gly Cys
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 71

His Ser Asp Ala Val Phe Thr Glu Asn Tyr Thr Lys Leu Arg Lys Gln
 1               5                  10                  15

Ala Ala Ala Lys Lys Tyr Leu Asn Ser Val Leu Thr Gly Gly Met
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 72

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Gly Ala
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 73

His Ser Asp Ala Val Phe Thr Glu Asn Tyr Thr Lys Leu Arg Lys Gln
 1               5                  10                  15

Xaa Ala Ala Lys Lys Tyr Leu Asn Ser Val Leu Thr Gly Gly Met
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
```

```
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 74

His Ser Asp Ala Val Phe Thr Asp Asn Tyr Thr Lys Leu Arg Lys Gln
 1               5                  10                  15

Xaa Ala Ala Lys Lys Tyr Leu Asn Ser Val Leu Thr Gly Gly Cys
            20                  25                  30

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 75

His Ser Asp Ala Val Phe Thr Glu Asn Tyr Thr Lys Leu Arg Lys Gln
 1               5                  10                  15

Xaa Ala Ala Lys Lys Tyr Leu Asn Ser Val Leu Thr Gly Gly Ser
            20                  25                  30

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle

<400> SEQUENCE: 76

His Ser Asp Ala Val Phe Thr Glu Asn Tyr Thr Lys Leu Arg Lys Gln
 1               5                  10                  15

Xaa Ala Ala Lys Lys Tyr Leu Asn Ser Val Leu Thr
            20                  25

<210> SEQ ID NO 77
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (17)
<223> OTHER INFORMATION: Nle

<400> SEQUENCE: 77
```

```
His Ser Asp Ala Val Phe Thr Glu Asn Tyr Thr Xaa Leu Arg Lys Gln
  1               5                  10                  15

Xaa Ala Val Lys Lys Tyr Leu Asn Ser Val Leu Thr
             20                  25

<210> SEQ ID NO 78
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 78

His Ser Asp Ala Val Phe Thr Asp Asn Tyr Thr Lys Leu Arg Lys Gln
  1               5                  10                  15

Xaa Ala Val Lys Lys Tyr Leu Asn Ala Leu Lys Lys Gly Gly Thr
             20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 79

His Ser Asp Ala Val Phe Thr Glu Asn Tyr Thr Lys Leu Arg Lys Gln
  1               5                  10                  15

Xaa Ala Val Lys Lys Tyr Leu Asn Ser Val Leu Thr Ala Ala Ala
             20                  25                  30

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 80

His Ser Asp Ala Val Phe Thr Asp Asn Tyr Thr Lys Leu Arg Lys Gln
  1               5                  10                  15

Ala Ala Ala Lys Lys Tyr Leu Asn Ser Val Leu Thr
             20                  25

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
```

<400> SEQUENCE: 81

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Lys
            20                  25                  30

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: p-NH2-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 82

His Ser Asp Ala Val Phe Thr Asp Asn Phe Thr Lys Leu Arg Lys Gln
 1               5                  10                  15

Xaa Ala Val Lys Lys Tyr Leu Asn Ser Val Leu Thr Gly Gly Cys
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 83

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Gly Cys
            20                  25                  30

<210> SEQ ID NO 84
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 84

His Ser Asp Ala Val Phe Thr Glu Asn Tyr Thr Lys Leu Arg Lys Gln
 1               5                  10                  15

```
Xaa Ala Val Lys Lys Tyr Leu Asn Ser Val Leu Thr Gly Gly Met
            20                  25                  30

<210> SEQ ID NO 85
<211> LENGTH: 27
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 85

Ser Asp Ala Val Phe Thr Asp Asn Tyr Thr Lys Leu Arg Lys Gln Xaa
 1               5                  10                  15

Ala Val Lys Lys Tyr Leu Asn Ser Val Leu Thr
            20                  25

<210> SEQ ID NO 86
<211> LENGTH: 27
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 86

Ser Asp Ala Val Phe Thr Asp Asn Tyr Thr Lys Leu Arg Lys Gln Xaa
 1               5                  10                  15

Ala Val Lys Lys Tyr Leu Asn Ser Val Leu Thr
            20                  25

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (1)
<223> OTHER INFORMATION: N-CH3-Ala
<220> FEATURE:
<221> NAME/KEY: MOD_RES
<222> LOCATION: (17)
<223> OTHER INFORMATION: Nle

<400> SEQUENCE: 87

Ala Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 88
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
```

```
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (31)
<223> OTHER INFORMATION: Cys(Acm)

<400> SEQUENCE: 88

His Ser Asp Ala Leu Phe Thr Asp Asn Tyr Thr Xaa Leu Arg Lys Gln
 1               5                  10                  15

Ala Ala Ala Lys Lys Tyr Leu Asn Thr Val Leu Thr Gly Gly Cys
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (10)
<223> OTHER INFORMATION: 2-Nal
<220> FEATURE:
<221> NAME/KEY: MOD_RES
<222> LOCATION: (17)
<223> OTHER INFORMATION: Nle

<400> SEQUENCE: 89

His Ser Asp Ala Val Phe Thr Asp Asn Xaa Thr Lys Leu Arg Lys Gln
 1               5                  10                  15

Xaa Ala Val Lys Lys Tyr Leu Asn Ser Val Leu Thr Gly Gly Met
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 90

His Ser Asp Ala Val Phe Thr Glu Asn Tyr Thr Lys Leu Lys Lys Gln
 1               5                  10                  15

Xaa Ala Ala Lys Lys Tyr Leu Asn Ser Val Leu Thr Gly Gly Cys
            20                  25                  30

<210> SEQ ID NO 91
<211> LENGTH: 31
<212> TYPE: PRT
```

```
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 91

His Ser Asp Ala Val Phe Thr Asp Asn Tyr Thr Lys Leu Arg Lys Gln
 1               5                  10                  15

Xaa Ala Ala Lys Lys Tyr Leu Asn Ser Val Leu Thr Gly Gly Cys
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (12)
<223> OTHER INFORMATION: Orn
<220> FEATURE:
<221> NAME/KEY: MOD_RES
<222> LOCATION: (31)
<223> OTHER INFORMATION: Cys(Acm)

<400> SEQUENCE: 92

His Ser Asp Ala Leu Phe Thr Asp Asn Tyr Thr Xaa Leu Arg Lys Gln
 1               5                  10                  15

Ala Ala Val Lys Lys Tyr Leu Asn Thr Val Leu Thr Gly Gly Cys
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 93

His Ser Asp Ala Val Phe Thr Glu Asn Tyr Thr Lys Leu Arg Lys Gln
 1               5                  10                  15

Xaa Ala Ala Lys Lys Tyr Leu Asn Ser Val Leu Thr Gly Gly Cys
            20                  25                  30
```

```
<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (1)
<223> OTHER INFORMATION: N-Me-Ala
<220> FEATURE:
<221> NAME/KEY: MOD_RES
<222> LOCATION: (17)
<223> OTHER INFORMATION: Nle

<400> SEQUENCE: 94

Ala Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (6)
<223> OTHER INFORMATION: p-F-Phe
<220> FEATURE:
<221> NAME/KEY: MOD_RES
<222> LOCATION: (10)
<223> OTHER INFORMATION: p-NH2-Phe
<220> FEATURE:
<221> NAME/KEY: MOD_RES
<222> LOCATION: (17)
<223> OTHER INFORMATION: Nle

<400> SEQUENCE: 95

His Ser Asp Ala Val Phe Thr Asp Asn Phe Thr Lys Leu Arg Lys Gln
 1               5                  10                  15

Xaa Ala Val Lys Lys Tyr Leu Asn Ser Val Leu Thr
            20                  25

<210> SEQ ID NO 96
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 96

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Gly Met
            20                  25                  30

<210> SEQ ID NO 97
<211> LENGTH: 28
<212> TYPE: PRT
```

```
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (10)
<223> OTHER INFORMATION: p-NH2-Phe
<220> FEATURE:
<221> NAME/KEY: MOD_RES
<222> LOCATION: (17)
<223> OTHER INFORMATION: Nle

<400> SEQUENCE: 97

His Ser Asp Ala Val Phe Thr Asp Asn Phe Thr Lys Leu Arg Lys Gln
 1               5                  10                  15

Xaa Ala Val Lys Lys Tyr Leu Asn Ser Val Leu Thr
            20                  25

<210> SEQ ID NO 98
<211> LENGTH: 31
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (31)
<223> OTHER INFORMATION: Cys(Acm)

<400> SEQUENCE: 98

His Ser Asp Ala Val Phe Thr Glu Asn Tyr Thr Lys Leu Arg Lys Gln
 1               5                  10                  15

Xaa Ala Val Lys Lys Tyr Leu Asn Ser Val Leu Thr Gly Gly Cys
            20                  25                  30

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle.sup.

<400> SEQUENCE: 99

His Ser Asp Ala Val Phe Thr Asp Asn Tyr Thr Arg Leu Arg Lys Gln
 1               5                  10                  15

Xaa Ala Val Lys Lys Tyr Leu Asn Ser Ile Leu Asn
            20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle.sup.
```

```
<400> SEQUENCE: 100

His Ser Asp Ala Val Phe Thr Asp Asn Tyr Thr Arg Leu Arg Lys Gln
 1               5                  10                  15

Xaa Ala Val Lys Lys Tyr Leu Asn Ser Ile Leu Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 101

His Ser Asp Ala Val Tyr Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 102

His Ser Asp Ala Val Phe Thr Asp Asn Tyr Thr Arg Leu Arg Lys Gln
 1               5                  10                  15

Met Ala Val Lys Lys Phe Leu Asn Ser Ile Leu Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 103

His Ser Asp Ala Val Phe Ser Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 104

His Ser Asp Ala Val Phe Lys Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 105
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 105

His Ser Asp Ala Val Phe Gln Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 106

His Ser Asp Ala Val Phe Asn Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 107

His Ser Asp Ala Val Phe Arg Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 108

His Ser Asp Ala Val Phe Thr Asp Arg Tyr Thr Arg Leu Arg Lys Gln
 1               5                  10                  15

Met Ala Val Lys Lys Tyr Leu Asn Ser Ile Leu Asn
            20                  25

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 109

His Ser Asp Ala Val Phe Thr Asp Gln Tyr Thr Arg Leu Arg Lys Gln
 1               5                  10                  15
```

Met Ala Val Lys Lys Tyr Leu Asn Ser Ile Leu Asn
            20                  25

<210> SEQ ID NO 110
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 110

His Ser Asp Ala Val Phe Thr Asp Lys Tyr Thr Arg Leu Arg Lys Gln
 1               5                  10                  15

Met Ala Val Lys Lys Tyr Leu Asn Ser Ile Leu Asn
            20                  25

<210> SEQ ID NO 111
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 111

His Ser Asp Ala Val Phe Thr Asp Leu Tyr Thr Arg Leu Arg Lys Gln
 1               5                  10                  15

Met Ala Val Lys Lys Tyr Leu Asn Ser Ile Leu Asn
            20                  25

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 112

His Ser Asp Ala Val Phe Thr Asp Ser Tyr Thr Arg Leu Arg Lys Gln
 1               5                  10                  15

Met Ala Val Lys Lys Tyr Leu Asn Ser Ile Leu Asn
            20                  25

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 113

His Ser Asp Ala Val Phe Thr Asp Thr Tyr Thr Arg Leu Arg Lys Gln
 1               5                  10                  15

Met Ala Val Lys Lys Tyr Leu Asn Ser Ile Leu Asn
            20                  25

<210> SEQ ID NO 114
<211> LENGTH: 28
<212> TYPE: PRT
<213> ORGANISM: Artificial Sequence
<220> FEATURE:
<223> OTHER INFORMATION: Description of Artificial Sequence: Synthetic VIP analog

<400> SEQUENCE: 114

His Ser Asp Ala Val Phe Thr Asp Asn Tyr Leu Arg Leu Arg Lys Gln
  1               5                  10                  15

Met Ala Val Lys Lys Tyr Leu Asn Ser Ile Leu Asn
             20                  25

<210> SEQ ID NO 115
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 115

His Ser Asp Ala Val Phe Thr Asp Asn Tyr Lys Arg Leu Arg Lys Gln
  1               5                  10                  15

Met Ala Val Lys Lys Tyr Leu Asn Ser Ile Leu Asn
             20                  25

<210> SEQ ID NO 116
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 116

His Ser Asp Ala Val Phe Thr Asp Asn Tyr Asn Arg Leu Arg Lys Gln
  1               5                  10                  15

Met Ala Val Lys Lys Tyr Leu Asn Ser Ile Leu Asn
             20                  25

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 117

His Ser Asp Ala Val Phe Thr Asp Asn Tyr Gln Arg Leu Arg Lys Gln
  1               5                  10                  15

Met Ala Val Lys Lys Tyr Leu Asn Ser Ile Leu Asn
             20                  25

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 118

His Ser Asp Ala Val Phe Thr Asp Asn Tyr Arg Arg Leu Arg Lys Gln
  1               5                  10                  15

Met Ala Val Lys Lys Tyr Leu Asn Ser Ile Leu Asn
             20                  25

```
<210> SEQ ID NO 119
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 119

His Ser Asp Ala Val Phe Thr Asp Asn Tyr Thr Arg Leu Arg Lys Thr
 1               5                  10                  15

Met Ala Val Lys Lys Tyr Leu Asn Ser Ile Leu Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 120

His Ser Asp Ala Val Phe Thr Asp Asn Tyr Thr Arg Leu Arg Lys Ser
 1               5                  10                  15

Met Ala Val Lys Lys Tyr Leu Asn Ser Ile Leu Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 121

His Ser Asp Ala Val Phe Thr Asp Asn Tyr Thr Arg Leu Arg Lys Leu
 1               5                  10                  15

Met Ala Val Lys Lys Tyr Leu Asn Ser Ile Leu Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 122

His Ser Asp Ala Val Phe Thr Asp Asn Tyr Thr Arg Leu Arg Lys Lys
 1               5                  10                  15

Met Ala Val Lys Lys Tyr Leu Asn Ser Ile Leu Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 123

His Ser Asp Ala Val Phe Thr Asp Asn Tyr Thr Arg Leu Arg Lys Asn
```

-continued

```
                1               5                  10                 15
Met Ala Val Lys Lys Tyr Leu Asn Ser Ile Leu Asn
            20                  25
```

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 124

```
His Ser Asp Ala Val Phe Thr Asp Asn Tyr Thr Arg Leu Arg Lys Arg
 1               5                  10                 15
Met Ala Val Lys Lys Tyr Leu Asn Ser Ile Leu Asn
            20                  25
```

<210> SEQ ID NO 125
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 125

```
His Ser Asp Ala Val Phe Thr Asp Asn Tyr Thr Arg Leu Arg Lys Gln
 1               5                  10                 15
Met Ala Val Lys Lys Tyr Leu Arg Ser Ile Leu Asn
            20                  25
```

<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 126

```
His Ser Asp Ala Val Phe Thr Asp Asn Tyr Thr Arg Leu Arg Lys Gln
 1               5                  10                 15
Met Ala Val Lys Lys Tyr Leu Gln Ser Ile Leu Asn
            20                  25
```

<210> SEQ ID NO 127
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 127

```
His Ser Asp Ala Val Phe Thr Asp Asn Tyr Thr Arg Leu Arg Lys Gln
 1               5                  10                 15
Met Ala Val Lys Lys Tyr Leu Lys Ser Ile Leu Asn
            20                  25
```

<210> SEQ ID NO 128
<211> LENGTH: 28
<212> TYPE: PRT
<213> ORGANISM: Artificial Sequence
<220> FEATURE:

<223> OTHER INFORMATION: Description of Artificial Sequence: Synthetic
      VIP analog

<400> SEQUENCE: 128

His Ser Asp Ala Val Phe Thr Asp Asn Tyr Thr Arg Leu Arg Lys Gln
 1               5                  10                  15

Met Ala Val Lys Lys Tyr Leu Leu Ser Ile Leu Asn
             20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 129

His Ser Asp Ala Val Phe Thr Asp Asn Tyr Thr Arg Leu Arg Lys Gln
 1               5                  10                  15

Met Ala Val Lys Lys Tyr Leu Ser Ser Ile Leu Asn
             20                  25

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 130

His Ser Asp Ala Val Phe Thr Asp Asn Tyr Thr Ser Leu Arg Lys Gln
 1               5                  10                  15

Met Ala Val Lys Lys Tyr Leu Asn Ser Ile Leu Asn
             20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 131

His Ser Asp Ala Val Phe Thr Asp Asn Tyr Thr Arg Leu Arg Lys Gln
 1               5                  10                  15

Met Ala Val Ser Lys Tyr Leu Asn Ser Ile Leu Asn
             20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (20)
<223> OTHER INFORMATION: Orn

<400> SEQUENCE: 132

His Ser Asp Ala Val Phe Thr Asp Asn Tyr Thr Arg Leu Arg Lys Gln
 1               5                  10                  15

Met Ala Val Xaa Lys Tyr Leu Asn Ser Ile Leu Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 133

His Ser Asp Ala Val Phe Thr Asp Asn Tyr Thr Arg Leu Arg Lys Gln
  1               5                  10                  15

Met Ala Val Arg Lys Tyr Leu Asn Ser Ile Leu Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 134

His Ser Asp Ala Val Phe Thr Asp Asn Tyr Thr Arg Leu Arg Lys Gln
  1               5                  10                  15

Met Ala Val Lys Lys Tyr Phe Asn Ser Ile Leu Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 135

His Ser Asp Ala Val Phe Thr Asp Asn Tyr Thr Arg Leu Arg Lys Gln
  1               5                  10                  15

Met Ala Val Lys Lys Tyr Leu Asn Ser Phe Leu Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 136

His Ser Asp Ala Val Phe Thr Asp Asn Tyr Thr Arg Tyr Arg Lys Gln
  1               5                  10                  15

Met Ala Val Lys Lys Tyr Leu Asn Ser Ile Leu Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic VIP analog

<400> SEQUENCE: 137

His Ser Asp Ala Val Phe Thr Asp Asn Tyr Thr Arg Leu Arg Lys Gln
 1               5                  10                  15

Met Ala Val Lys Lys Tyr Tyr Asn Ser Ile Leu Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 138

His Ser Asp Ala Val Phe Thr Asp Asn Tyr Thr Arg Leu Arg Lys Gln
 1               5                  10                  15

Met Ala Val Lys Lys Tyr Leu Asn Ser Tyr Leu Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 139

His Ser Asp Ala Val Phe Thr Asp Asn Tyr Thr Arg Leu Arg Lys Gln
 1               5                  10                  15

Met Ala Val Lys Lys Tyr Leu Asn Ser Leu Leu Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 140

His Ser Asp Ala Val Phe Thr Asp Asn Tyr Thr Arg Ile Arg Lys Gln
 1               5                  10                  15

Met Ala Val Lys Lys Tyr Leu Asn Ser Ile Leu Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 141

His Ser Asp Ala Val Phe Thr Asp Asn Tyr Thr Arg Leu Arg Lys Gln
 1               5                  10                  15

Met Ala Val Lys Lys Tyr Ile Asn Ser Ile Leu Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 142

His Ser Asp Ala Val Phe Thr Asp Asn Tyr Thr Arg Val Arg Lys Gln
 1               5                  10                  15

Met Ala Val Lys Lys Tyr Leu Asn Ser Ile Leu Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 143

His Ser Asp Ala Val Phe Thr Asp Asn Tyr Thr Arg Leu Arg Lys Gln
 1               5                  10                  15

Met Ala Val Lys Lys Tyr Val Asn Ser Ile Leu Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (13)
<223> OTHER INFORMATION: Nle

<400> SEQUENCE: 144

His Ser Asp Ala Val Phe Thr Asp Asn Tyr Thr Arg Xaa Arg Lys Gln
 1               5                  10                  15

Met Ala Val Lys Lys Tyr Leu Asn Ser Ile Leu Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (23)
<223> OTHER INFORMATION: Nle

<400> SEQUENCE: 145

His Ser Asp Ala Val Phe Thr Asp Asn Tyr Thr Arg Leu Arg Lys Gln
 1               5                  10                  15

Met Ala Val Lys Lys Tyr Xaa Asn Ser Ile Leu Asn
            20                  25

<210> SEQ ID NO 146
<211> LENGTH: 28
<212> TYPE: PRT

-continued

```
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (26)
<223> OTHER INFORMATION: Nle

<400> SEQUENCE: 146

His Ser Asp Ala Val Phe Thr Asp Asn Tyr Thr Arg Leu Arg Lys Gln
  1               5                  10                  15

Met Ala Val Lys Lys Tyr Leu Asn Ser Xaa Leu Asn
             20                  25

<210> SEQ ID NO 147
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 147

His Ser Asp Ala Val Phe Thr Asp Asn Tyr Thr Arg Leu Arg Lys Gln
  1               5                  10                  15

Met Ala Val Lys Arg Tyr Leu Asn Ser Ile Leu Asn
             20                  25

<210> SEQ ID NO 148
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 148

His Ser Asp Ala Val Phe Thr Asp Asn Tyr Thr Arg Leu Leu Lys Gln
  1               5                  10                  15

Met Ala Val Lys Lys Tyr Leu Asn Ser Ile Leu Asn
             20                  25

<210> SEQ ID NO 149
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 149

His Ser Asp Ala Val Phe Thr Asp Asn Tyr Thr Arg Leu Arg Lys Gln
  1               5                  10                  15

Met Ala Val Lys Leu Tyr Leu Asn Ser Ile Leu Asn
             20                  25

<210> SEQ ID NO 150
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (14)
```

<223> OTHER INFORMATION: Orn

<400> SEQUENCE: 150

His Ser Asp Ala Val Phe Thr Asp Asn Tyr Thr Arg Leu Xaa Lys Gln
 1               5                  10                  15

Met Ala Val Lys Lys Tyr Leu Asn Ser Ile Leu Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (21)
<223> OTHER INFORMATION: Orn

<400> SEQUENCE: 151

His Ser Asp Ala Val Phe Thr Asp Asn Tyr Thr Arg Leu Arg Lys Gln
 1               5                  10                  15

Met Ala Val Lys Xaa Tyr Leu Asn Ser Ile Leu Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (14)
<223> OTHER INFORMATION: Nle

<400> SEQUENCE: 152

His Ser Asp Ala Val Phe Thr Asp Asn Tyr Thr Arg Leu Xaa Lys Gln
 1               5                  10                  15

Met Ala Val Lys Lys Tyr Leu Asn Ser Ile Leu Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (21)
<223> OTHER INFORMATION: Nle

<400> SEQUENCE: 153

His Ser Asp Ala Val Phe Thr Asp Asn Tyr Thr Arg Leu Arg Lys Gln
 1               5                  10                  15

Met Ala Val Lys Xaa Tyr Leu Asn Ser Ile Leu Asn
            20                  25

<210> SEQ ID NO 154
<211> LENGTH: 28
<212> TYPE: PRT
<213> ORGANISM: Artificial Sequence
<220> FEATURE:

-continued

<223> OTHER INFORMATION: Description of Artificial Sequence: Synthetic
      VIP analog

<400> SEQUENCE: 154

His Ser Asp Ala Val Phe Thr Asp Asn Tyr Thr Arg Leu Arg Arg Gln
1               5                   10                  15

Met Ala Val Lys Lys Tyr Leu Asn Ser Ile Leu Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 155

His Ser Asp Ala Val Phe Thr Asp Asn Tyr Thr Arg Leu Arg Ser Gln
1               5                   10                  15

Met Ala Val Lys Lys Tyr Leu Asn Ser Ile Leu Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 156

His Ser Asp Ala Val Phe Thr Asp Asn Tyr Thr Arg Leu Arg Gln Gln
1               5                   10                  15

Met Ala Val Lys Lys Tyr Leu Asn Ser Ile Leu Asn
            20                  25

<210> SEQ ID NO 157
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (15)
<223> OTHER INFORMATION: Orn

<400> SEQUENCE: 157

His Ser Asp Ala Val Phe Thr Asp Asn Tyr Thr Arg Leu Arg Xaa Gln
1               5                   10                  15

Met Ala Val Lys Lys Tyr Leu Asn Ser Ile Leu Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 158

His Ser Asp Ala Val Phe Thr Asp Asn Tyr Thr Arg Leu Arg Lys Gln
1               5                   10                  15

```
Met Ala Met Lys Lys Tyr Leu Asn Ser Ile Leu Asn
            20                  25
```

<210> SEQ ID NO 159
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 159

```
His Ser Asp Ala Val Phe Thr Asp Asn Tyr Thr Arg Leu Arg Lys Gln
 1               5                  10                  15
Leu Ala Val Lys Lys Tyr Leu Asn Ser Ile Leu Asn
            20                  25
```

<210> SEQ ID NO 160
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 160

```
His Ser Asp Ala Val Phe Thr Asp Asn Tyr Thr Arg Leu Arg Lys Gln
 1               5                  10                  15
Met Ala Leu Lys Lys Tyr Leu Asn Ser Ile Leu Asn
            20                  25
```

<210> SEQ ID NO 161
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 161

```
His Ser Asp Ala Val Phe Thr Asp Asn Tyr Thr Arg Leu Arg Lys Gln
 1               5                  10                  15
Val Ala Val Lys Lys Tyr Leu Asn Ser Ile Leu Asn
            20                  25
```

<210> SEQ ID NO 162
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 162

```
His Ser Asp Ala Val Phe Thr Asp Asn Tyr Thr Arg Leu Arg Lys Gln
 1               5                  10                  15
Lys Ala Val Lys Lys Tyr Leu Asn Ser Ile Leu Asn
            20                  25
```

<210> SEQ ID NO 163
<211> LENGTH: 28
<212> TYPE: PRT
<213> ORGANISM: Artificial Sequence
<220> FEATURE:
<223> OTHER INFORMATION: Description of Artificial Sequence: Synthetic VIP analog

<400> SEQUENCE: 163

His Ser Asp Ala Val Phe Thr Asp Asn Tyr Thr Arg Leu Arg Lys Gln
 1               5                  10                  15

Met Ala Lys Lys Lys Tyr Leu Asn Ser Ile Leu Asn
            20                  25

<210> SEQ ID NO 164
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 164

His Ser Asp Ala Val Phe Thr Asp Asn Tyr Thr Arg Leu Arg Lys Gln
 1               5                  10                  15

Ile Ala Val Lys Lys Tyr Leu Asn Ser Ile Leu Asn
            20                  25

<210> SEQ ID NO 165
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 165

His Ser Asp Ala Val Phe Thr Asp Asn Tyr Thr Arg Leu Arg Lys Gln
 1               5                  10                  15

Met Ala Ile Lys Lys Tyr Leu Asn Ser Ile Leu Asn
            20                  25

<210> SEQ ID NO 166
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (19)
<223> OTHER INFORMATION: Nle

<400> SEQUENCE: 166

His Ser Asp Ala Val Phe Thr Asp Asn Tyr Thr Arg Leu Arg Lys Gln
 1               5                  10                  15

Met Ala Xaa Lys Lys Tyr Leu Asn Ser Ile Leu Asn
            20                  25

<210> SEQ ID NO 167
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 167

His Ser Asp Ala Val Phe Thr Asp Asn Tyr Thr Arg Leu Arg Lys Gln
 1               5                  10                  15

```
Met Leu Val Lys Lys Tyr Leu Asn Ser Ile Leu Asn
            20                  25

<210> SEQ ID NO 168
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 168

His Ser Asp Ala Val Phe Thr Asp Asn Tyr Thr Arg Leu Arg Lys Gln
 1               5                  10                  15

Met Ala Val Lys Lys Tyr Leu Asn Asn Ile Leu Asn
            20                  25

<210> SEQ ID NO 169
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 169

His Ser Asp Ala Val Phe Thr Asp Asn Tyr Thr Arg Leu Arg Lys Gln
 1               5                  10                  15

Met Ala Val Lys Lys Tyr Leu Asn Leu Ile Leu Asn
            20                  25

<210> SEQ ID NO 170
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> S

```
<400> SEQUENCE: 172

His Ser Phe Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 173
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 173

His Ser Tyr Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 174
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 174

His Ser Asp Ala Val Phe Phe Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 175
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 175

His Ser Asp Ala Val Phe Tyr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 176

His Ser Asp Ala Val Phe Thr Asp Asn Tyr Thr Arg Leu Arg Lys Gln
 1               5                  10                  15

Met Ala Phe Lys Lys Tyr Leu Asn Ser Ile Leu Asn
            20                  25

<210> SEQ ID NO 177
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 177

His Ser Asp Ala Val Phe Thr Asp Asn Tyr Thr Arg Leu Arg Lys Gln
 1               5                  10                  15

Met Ala Tyr Lys Lys Tyr Leu Asn Ser Ile Leu Asn
            20                  25

<210> SEQ ID NO 178
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 178

His Ser Asp Thr Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 179
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 179

His Ser Asp Ser Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 180

His Ser Asp Asn Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 181
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 181

His Ser Asp Gln Val Phe Thr Asp Asn Tyr Thr Arg Leu Arg Lys Gln
 1               5                  10                  15
```

Met Ala Val Lys Lys Tyr Leu Asn Ser Ile Leu Asn
            20                  25

<210> SEQ ID NO 182
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 182

His Ser Asp Ala Val Thr Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 183
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 183

His Ser Asp Ala Val Ser Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 184
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 184

His Ser Asp Ala Val Asn Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 185
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 185

His Ser Asp Ala Val Gln Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 186
<211> LENGTH: 28
<212> TYPE: PRT
<213> ORGANISM: Artificial Sequence
<220> FEATURE:
<223> OTHER INFORMATION: Description of Artificial Sequence: Synthetic VIP analog

<400> SEQUENCE: 186

His Ser Asp Ala Val Ala Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 187
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 187

His Ser Asp Ala Val Phe Thr Thr Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 188
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 188

His Ser Asp Ala Val Phe Thr Ser Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 189
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 189

His Ser Asp Ala Val Phe Thr Asn Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 190
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 190

His Ser Asp Ala Val Phe Thr Gln Asn Tyr Thr Arg Leu Arg Lys Gln
  1               5                  10                  15

Met Ala Val Lys Lys Tyr Leu Asn Ser Ile Leu Asn
             20                  25

```
<210> SEQ ID NO 191
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 191

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Ser
            20                  25

<210> SEQ ID NO 192
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 192

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Gln
            20                  25

<210> SEQ ID NO 193
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 193

His Ser Asp Ala Val Phe Thr Asp Asn Tyr Thr Gln Leu Arg Lys Gln
 1               5                  10                  15

Met Ala Val Lys Lys Tyr Leu Asn Ser Ile Leu Asn
            20                  25

<210> SEQ ID NO 194
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 194

His Ser Asp Ala Val Phe Thr Asp Asn Tyr Thr Arg Leu Arg Lys Gln
 1               5                  10                  15

Met Ala Val Gln Lys Tyr Leu Asn Ser Ile Leu Asn
            20                  25

<210> SEQ ID NO 195
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 195

His Ser Asp Ala Val Phe Thr Asp Asn Tyr Thr Arg Leu Arg Lys Gln
```

```
               1               5                  10                 15
Met Ala Val Lys Ser Tyr Leu Asn Ser Ile Leu Asn
                20                 25
```

<210> SEQ ID NO 196
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 196

```
His Ser Asp Ala Val Phe Thr Asp Asn Tyr Thr Arg Leu Arg Lys Gln
 1               5                  10                 15
Met Ala Val Lys Gln Tyr Leu Asn Ser Ile Leu Asn
                20                 25
```

<210> SEQ ID NO 197
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 197

```
His Ser Asp Ala Val Phe Thr Asp Asn Tyr Thr Arg Met Arg Lys Gln
 1               5                  10                 15
Met Ala Val Lys Lys Tyr Leu Asn Ser Ile Leu Asn
                20                 25
```

<210> SEQ ID NO 198
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 198

```
His Ser Asp Ala Val Phe Thr Asp Asn Tyr Thr Arg Leu Arg Lys Gln
 1               5                  10                 15
Ile Ala Val Lys Lys Tyr Leu Asn Ser Ile Leu Asn
                20                 25
```

<210> SEQ ID NO 199
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 199

```
His Ser Asp Ala Val Phe Thr Asp Asn Tyr Thr Arg Leu Arg Lys Gln
 1               5                  10                 15
Met Ala Val Lys Lys Tyr Met Asn Ser Ile Leu Asn
                20                 25
```

<210> SEQ ID NO 200
<211> LENGTH: 28
<212> TYPE: PRT
<213> ORGANISM: Artificial Sequence
<220> FEATURE:

<223> OTHER INFORMATION: Description of Artificial Sequence: Synthetic
      VIP analog

<400> SEQUENCE: 200

His Ser Asp Ala Val Phe Thr Asp Asn Tyr Thr Arg Leu Arg Lys Gln
  1               5                  10                  15

Met Ala Val Lys Lys Tyr Leu Asn Ser Met Leu Asn
             20                  25

<210> SEQ ID NO 201
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 201

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Thr
             20                  25

<210> SEQ ID NO 202
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analog
<220> FEATURE:
<221> NAME/KEY: MOD_RES
<222> LOCATION: (17)
<223> OTHER INFORMATION: Nle

<400> SEQUENCE: 202

His Ser Asp Ala Val Phe Thr Asp Asn Tyr Thr Lys Leu Arg Lys Gln
  1               5                  10                  15

Xaa Ala Val Lys Lys Tyr Leu Asn Ser Ala Ala Thr
             20                  25

<210> SEQ ID NO 203
<211> LENGTH: 30
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 203

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn Gly Cys
             20                  25                  30

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 204

His Ser Asp Ala Val Phe Thr Asp Asn Tyr Thr Arg Leu Arg Lys Gln
  1               5                  10                  15

```
Met Ala Val Lys Lys Tyr Leu Asn Ser Ile Leu Asn Gly Cys
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: Description of Artificial Sequence: Synthetic
      VIP analog

<400> SEQUENCE: 205

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn Gly Cys
            20                  25                  30

<210> SEQ ID NO 206
<211> LENGTH: 4
<212> TYPE: PRT
<213> ORGANISM: Unknown Organism
<220> FEATURE:
<223> OTHER INFORMATION: Description of Unknown Organism: Melanocortin
      peptide

<400> SEQUENCE: 206

His Phe Arg Trp
 1

<210> SEQ ID NO 207
<211> LENGTH: 28
<212> TYPE: PRT
<213> ORGANISM: Artificial Sequence
<220> FEATURE:
<223> OTHER INFORMATION: Description of Artificial Sequence: Synthetic
      VIP analogs
<220> FEATURE:
<221> NAME/KEY: MOD_RES
<222> LOCATION: (17)
<223> OTHER INFORMATION: Nle

<400> SEQUENCE: 207

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Ala
            20                  25
```